(12) United States Patent
Ayliffe

(10) Patent No.: US 8,171,778 B2
(45) Date of Patent: *May 8, 2012

(54) THIN FILM PARTICLE SENSOR

(75) Inventor: Harold E. Ayliffe, Woodinville, WA (US)

(73) Assignee: E I Spectra, LLC, Woodinville, WA (US)

( * ) Notice: Subject to any disclaimer, the term of this patent is extended or adjusted under 35 U.S.C. 154(b) by 584 days.

This patent is subject to a terminal disclaimer.

(21) Appl. No.: 12/381,252

(22) Filed: Mar. 10, 2009

(65) Prior Publication Data

US 2009/0272179 A1 Nov. 5, 2009

Related U.S. Application Data

(63) Continuation-in-part of application No. 11/800,167, filed on May 4, 2007, now Pat. No. 7,520,164.

(60) Provisional application No. 60/798,155, filed on May 5, 2006.

(51) Int. Cl.
*G01N 15/06* (2006.01)
*G01N 27/00* (2006.01)

(52) U.S. Cl. ...................................... 73/61.71; 324/71.1

(58) Field of Classification Search .................. 73/61.41, 73/61.71; 324/71.1
See application file for complete search history.

(56) References Cited

U.S. PATENT DOCUMENTS

| | | | |
|---|---|---|---|
| 2,656,508 A | 10/1953 | Coulter | |
| 5,126,022 A | 6/1992 | Soane et al. | 204/458 |
| 5,338,427 A | 8/1994 | Shartle et al. | 204/604 |
| 5,376,878 A | 12/1994 | Fisher | |
| 5,459,406 A | 10/1995 | Louge | 324/688 |
| 5,800,690 A | 9/1998 | Chow et al. | 204/451 |
| 5,933,707 A | 8/1999 | Ayliffe et al. | 438/107 |
| 6,045,676 A | 4/2000 | Mathies et al. | 204/603 |
| 6,091,975 A | 7/2000 | Daddona et al. | 600/345 |
| 6,169,394 B1 | 1/2001 | Frazier et al. | |
| 6,426,615 B1 | 7/2002 | Mehta | |
| 6,437,551 B1 | 8/2002 | Krulevitch et al. | |
| 6,440,725 B1 | 8/2002 | Pourahmadi et al. | 435/288.5 |
| 6,454,945 B1 | 9/2002 | Weigl et al. | |
| 6,488,896 B2 | 12/2002 | Weigl et al. | |
| 6,638,482 B1 | 10/2003 | Ackley et al. | 422/68.1 |
| 6,656,431 B2 | 12/2003 | Holl et al. | |
| 6,674,525 B2 | 1/2004 | Bardell et al. | 356/246 |
| 6,703,819 B2 | 3/2004 | Gascoyne et al. | |
| 6,794,877 B2 | 9/2004 | Blomberg et al. | |
| 7,204,139 B2 | 4/2007 | Takayama | 73/204.26 |
| 7,223,363 B2 | 5/2007 | McNeely et al. | 422/58 |
| 7,235,400 B2 | 6/2007 | Adey | 435/287.2 |

(Continued)

*Primary Examiner* — John Fitzgerald
(74) *Attorney, Agent, or Firm* — Brian C. Trask

(57) ABSTRACT

A Coulter-style, microfluidic sensor formed by stacking a plurality of substantially non-electrically conductive layers, typically formed from thin polymer films. Certain layers carry patterned electrodes that are arranged to permit their connection to an electrical interrogation circuit. Electrodes may be disposed in a 3-dimensional array in the sensor. A fluid path through the sensor includes an orifice sized to promote single-file travel of particles. The orifice may be defined by a tunnel passing through at least one layer. Particles entrained in an electrolytic carrier fluid may be detected, or otherwise characterized, by interrogation circuitry connected to the sensor. Certain sensors may include portions of a fluid path disposed parallel to the layers. In certain preferred embodiments, the sensor is carried by a cartridge, which is adapted to couple with an interrogation platform. Desirably, such coupling places the sensor in-circuit with operable interrogation electronics, as well as with a fluid-flow control device. Structure included in a cartridge may provide fluid sample loading, routing, and storage capabilities.

20 Claims, 17 Drawing Sheets

U.S. PATENT DOCUMENTS

| | | | |
|---|---|---|---|
| 7,332,902 B1 | 2/2008 | Vermeire et al. | 324/71.4 |
| 7,417,418 B1 | 8/2008 | Ayliffe | 324/71.1 |
| 7,520,164 B1 * | 4/2009 | Ayliffe | 73/61.71 |
| 7,579,823 B1 * | 8/2009 | Ayliffe | 324/71.1 |
| 2002/0117517 A1 | 8/2002 | Unger et al. | |
| 2002/0149766 A1 | 10/2002 | Bardell et al. | 356/246 |
| 2004/0037739 A1 | 2/2004 | McNeely et al. | 422/58 |
| 2005/0054078 A1 | 3/2005 | Miller et al. | 435/287.1 |
| 2005/0118705 A1 | 6/2005 | Rabbitt et al. | 435/287.1 |
| 2005/0255600 A1 | 11/2005 | Padmanabhan et al. | 436/63 |

\* cited by examiner

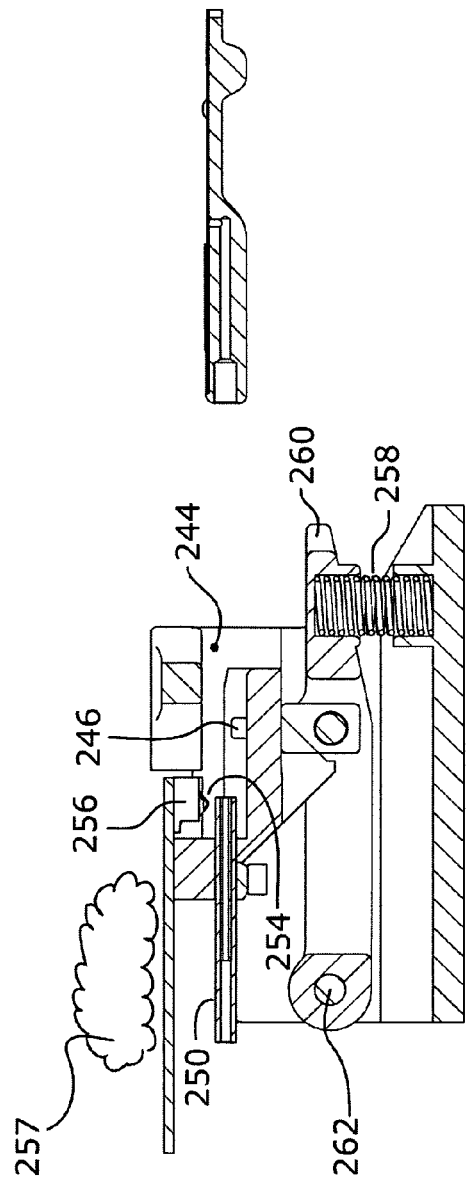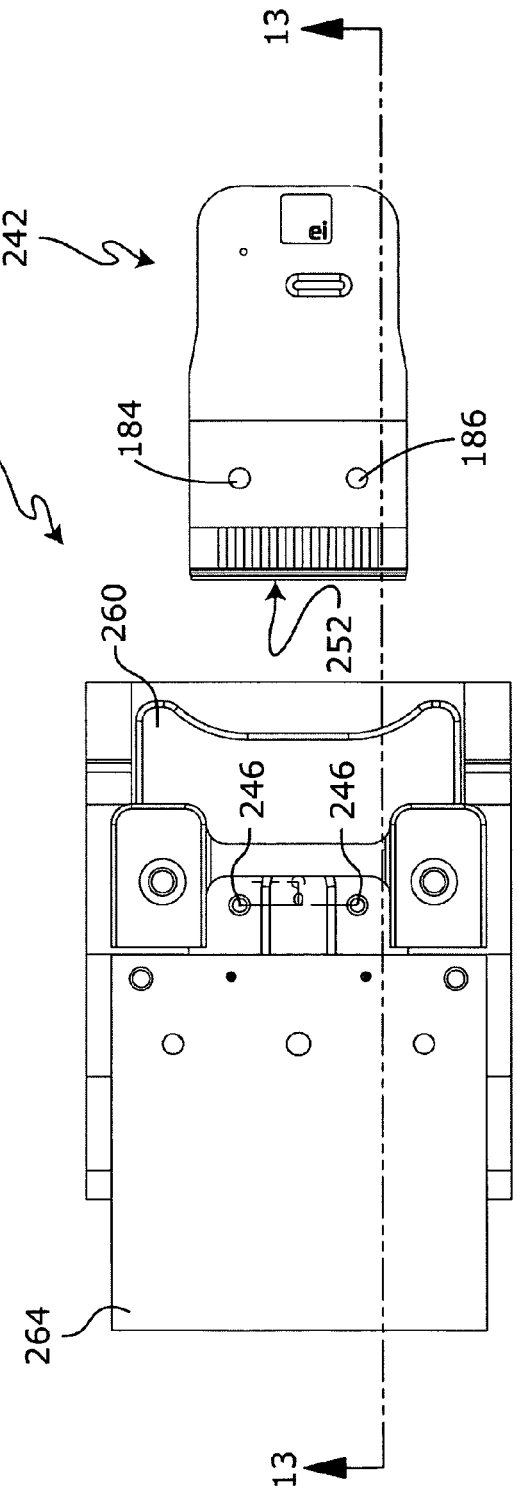

THIN FILM PARTICLE SENSOR

RELATED APPLICATIONS

This application is a continuation-in-part of U.S. utility application Ser. No. 11/800,167, filed May 4, 2007 now U.S. Pat. No. 7,520,164 and claims the benefit under 35 U.S.C. 119(e) of the filing date of Provisional Application Ser. No. 60/798,155, filed May 5, 2006, for "Thin film particle sensor", the entire disclosures of which are incorporated by reference.

BACKGROUND

1. Field of the Invention

This invention relates generally to electrically-based sensors for use in detecting, quantifying, qualifying, or otherwise sensing, particles carried by a fluid. It is particularly directed to an improved microfluidic sensor and interrogation structure for such particle sensing application.

2. State of the Art

Pioneering work in particle detection by measuring impedance deviation caused by particles flowing through a small aperture between two containers of electrically conductive fluid is disclosed in U.S. Pat. No. 2,656,508 to W. H, Coulter. Coulter's name is now associated with the principle of particles causing a change in electric impedance as they occlude a portion of the aperture. Since publication of his patent, considerable effort has been devoted to developing and refining sensing devices operating under the Coulter principle. Relevant U.S. patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. No. 6,454,945 and U.S. Pat. No. 6,488,896 to Weigl et al., U.S. Pat. No. 6,656,431 to Holl et al., and U.S. Pat. No. 6,794,877 to Blomberg et al. Patent application 2002/117,517 to Unger et al. is also relevant. Each above-referenced document is hereby incorporated by reference, as though set forth herein in their entireties, for their disclosures of relevant technology and structure employed in various sensor arrangements.

While considerable progress has been made in sensor technology, a need remains for sensors adapted to interrogate particles that are entrained in a conductive fluid, which are low in cost, permit sample manipulation, and/or ensure accurate selection of a sample volume. It would be an improvement to provide a sensitive and accurate sensor embodied on a cartridge that is sufficiently low in cost to permit its disposal after a single use. It would be another improvement to provide such a cartridge structured to permit interrogation of a defined sample volume. Still further improvements would provide verification of sample presence at one or more desired position in the sensor, and permit estimation of the flow rate of the sample.

BRIEF SUMMARY OF THE INVENTION

This invention provides certain electrically active sensors and methods of use of those sensors. One operable embodiment of such sensors includes a sensor component formed from a plurality of stacked planar thin film layers. Certain of the layers carry one or more electrode to dispose a plurality of electrical conductors in a 3-dimensional array in space. A first portion of a fluid path disposed inside an exemplary sensor passes through at least one layer. A second portion of the fluid path and a third portion of the fluid path are disposed parallel to, and within, the layers, and are disposed on opposite sides of a particle interrogation zone. Desirably, structure associated with the first portion is sized to urge particles entrained in a carrier fluid into substantially single-file travel through the particle interrogation zone.

Certain preferred embodiments include a first electrode having a surface greater than about $\frac{1}{5}$ cm$^2$ disposed for contact with fluid in the second portion, and a second electrode having a surface greater than about $\frac{1}{5}$ cm$^2$ disposed for contact with fluid in the third portion of the fluid path. A sensor may sometimes include a third electrode disposed downstream from the first electrode, and a fourth electrode disposed downstream from the third electrode. In such case, the particle interrogation zone typically comprises a volume disposed between the third electrode and fourth electrode. Operable sensors may be constructed having one, two, three, four, or more electrodes.

A sensor may also include flow termination structure disposed downstream from the interrogation zone. Operable flow termination structure is arranged to resist further flow of fluid through the interrogation zone subsequent to e.g. processing a sample having a known volumetric size.

A sensor may include fluid detection structure arranged to permit nonvisual verification of presence of sample fluid at one or more location in the sensor. Sometimes, a sensor may include flow detection structure arranged to permit estimation of rate-of-flow of sample fluid downstream from the interrogation zone. Certain sensors include a particle filter disposed upstream of the interrogation zone. An operable such filter includes openings sized smaller than a cross-section of the interrogation zone.

A method of use of the apparatus includes: infusing a dose of fluid into a receiving chamber associated with a sensor; applying a fluid motive source to the sensor effective to cause fluid from the dose to flow through the sensor; applying an electric stimulation signal to stimulated electrodes of the sensor and detecting an electric data signal received from at least one interrogation electrode associated with the interrogation zone; activating a fluid detection portion of the sensor effective to determine arrival of a wave-front of the dose at a first location disposed downstream of the interrogation zone; and monitoring the data signal as fluid from the dose continues to flow through the interrogation zone. In certain cases, additional fluid flow through the interrogation zone is automatically resisted by structure of the sensor subsequent to processing a portion of the dose having a known volumetric size. The method may also include detecting the wave-front at a second location spaced apart downstream from the first location by a known volume; and estimating the volumetric flow rate of the dose. Detection of a fluid wave-front at particular locations in the sensor may sometimes be used as triggering events for certain activity, such as starting and stopping collection of data.

The device may be embodied as a multi-layer microfluidic sensor. In an exemplary such embodiment, a first fluid-flow channel is formed in a first layer, with the first fluid-flow channel being configured to permit fluid flow in a direction generally parallel to the first layer, and a depth of the channel being less than about 2 mm. A first electrode of such exemplary embodiment is disposed for contact with fluid in the first fluid-flow channel. A second electrode is disposed downstream of the first electrode. A second fluid-flow channel passes through a second layer, with the second fluid-flow channel being sized to urge substantially single-file travel there-through of particles entrained in a carrier fluid. A third electrode is disposed for contact with fluid in a third fluid-flow channel, with the third fluid-flow channel being formed in a third layer and configured to permit flow of fluid received from the second fluid-flow channel to continue in a direction generally parallel to the third layer. Desirably, the first electrode and second electrode are carried on a first side of the second layer; and the third electrode is carried on a second side of the second layer. The multi-layer sensor may include a fourth electrode disposed to cooperate with the first, second, and third electrodes. Desirably, the first electrode and second electrode are carried on a first side of an interrogation layer, and the third electrode and fourth electrode are carried on a second side of the interrogation layer.

An operable interrogation layer may include the second layer, only, or additional layers also. It is within contemplation for certain operable embodiments to provide only a single particle detecting electrode disposed downstream of the interrogation zone, in which case a stimulus signal may be applied to the electrolytic fluid at a location remote from the sensor. It is further within contemplation for certain operable embodiments to provide a particle detecting electrode arrangement including an electrode disposed on each side of the interrogation zone.

A multi-layer sensor may also include a first cap layer configured and arranged to provide a boundary surface for the first fluid-flow channel, and a second cap layer configured and arranged to provide a boundary surface for the third fluid-flow channel. In such case, a first fluid via passing through the first cap layer is typically configured and arranged for communication with the first fluid-flow channel to permit introduction of sample fluid into the sensor. Also, a second fluid via passing through the second layer is typically configured and arranged to permit fluid communication from the third fluid-flow channel to an exit from the sensor. It is within contemplation for a layer to be embossed to provide fluid channel structure. In certain sensors, fluid enters a thin film portion of the sensor through an entrance port and exits the sensor through an exit port, with the entrance port and exit port being disposed on the same side of the thin film portion. A sensor may include fluid detection structure arranged to permit non-visual verification of presence of sample fluid downstream of the third electrode. A sensor may include flow detection structure arranged to permit estimation of rate-of-flow of sample fluid downstream of the third electrode. A sensor may include holding structure adapted to receive sample fluid effective to define a volumetric size of a processed sample. One operable holding structure includes a dead-end chamber defining, in harmony with trigger structure of the sensor, a known volume and being vented through a fluid barrier effective to resist further flow of fluid through the sensor subsequent to filling of the chamber.

A device constructed according to certain principles of the instant invention forms a microfluidic sensor including electrodes adapted to characterize particles entrained in a fluid. Such sensor includes a plurality of stacked planar thin film layers cooperatively configured to define a fluid conduit through the sensor. Preferably, a constriction portion of the fluid conduit is sized to urge particles into substantially single-file travel through a particle interrogation zone. A first pair of electrodes may be disposed upstream of the constriction portion; and a second pair of electrodes may be disposed downstream of the constriction portion. Desirably, the first pair of electrodes is carried on one side of a first layer of the sensor, and least one electrode of the second pair of electrodes is carried on the opposite side of the first layer. Such sensor may also include a flow termination structure configured and arranged to resist further flow of fluid through the interrogation zone subsequent to processing a dose of fluid having a known volume.

Sometimes, the sensor may include first fluid detection structure arranged to determine arrival of a wave-front of fluid at a first location inside the conduit. Certain sensors may also include second fluid detection structure arranged to determine arrival of a wave-front of fluid at a second location disposed downstream from the first location, with the first location and second location being spaced apart by a stretch of conduit having a known volume. Sometimes, the first location is disposed downstream from the interrogation zone. Sometimes, the first location may be disposed downstream from all electrodes operable on the interrogation zone.

BRIEF DESCRIPTION OF THE DRAWINGS

In the drawings, which illustrate what are currently considered to be the best modes for carrying out the invention:

FIG. 12 is a top view of a cartridge in position for its installation into an interrogation platform;

FIG. 13 is a cross-section view, taken through section 13-13 in FIG. 12, and looking in the direction of the arrows;

DETAILED DESCRIPTION OF THE ILLUSTRATED EMBODIMENT(S)

Figure 1:
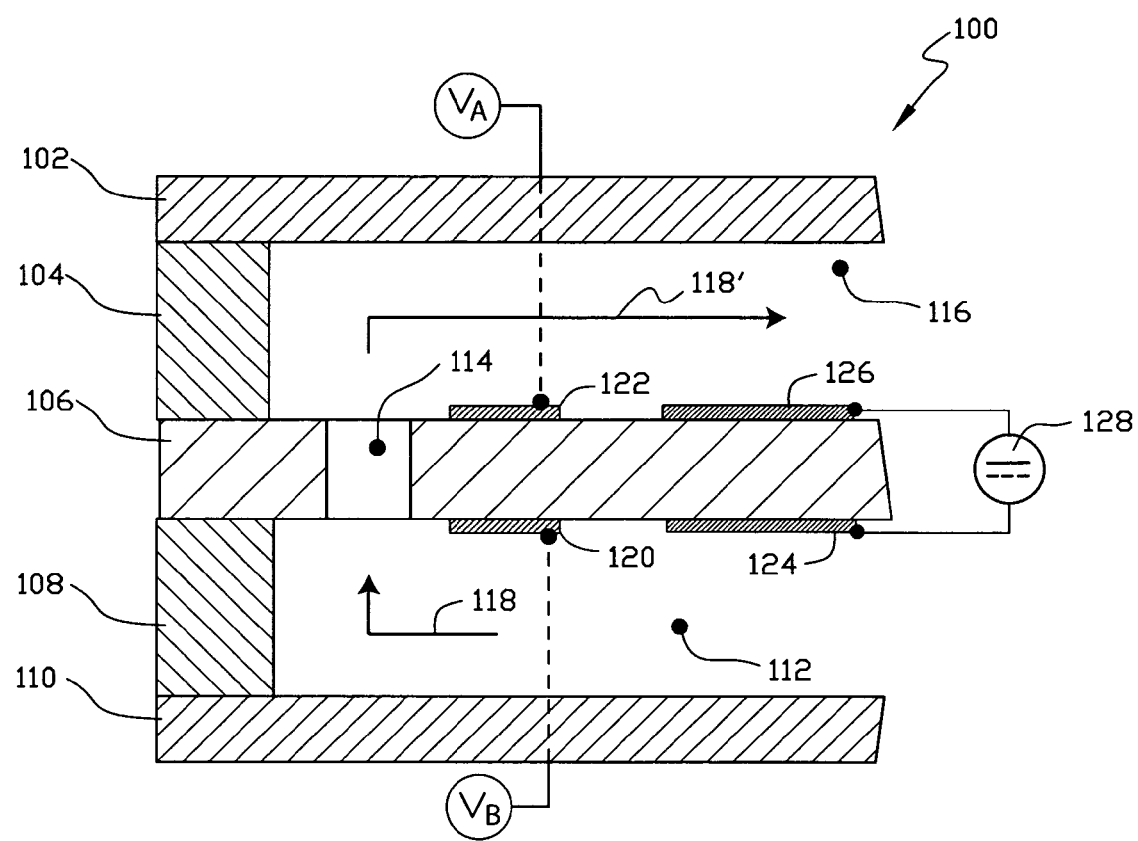
FIG. 1 is a cross-section schematic of a multi-layer sensor component structured according to certain principles of the instant invention.

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

Currently preferred embodiments of the present invention provide low-cost, disposable, sensors operable to perform analyses of various sorts on particles that are carried in a fluid. Sensors structured according to certain principles of the instant invention may be used once, and discarded. However, it is within contemplation that such sensors may alternatively be reused a number of times.

Examples of analyses in which embodiments of the invention may be used to advantage include, without limitation, counting, characterizing, or detecting members of any cultured cells, and in particular blood cell analyses such as counting red blood cells (RBCs) and/or white blood cells (WBCs), complete blood counts (CBCs), CD4/CD8 white blood cell counting for HIV+ individuals; whole milk analysis; sperm count in semen samples; and generally those analyses involving numerical evaluation or particle size distribution for a particle-bearing fluid (including nonbiological). Embodiments of the invention may be used to provide rapid and point-of-care testing, including home market blood diagnostic tests. Certain embodiments may be used as an automated laboratory research cell counter to replace manual hemacytometry. It is within contemplation to combine the instant invention with additional diagnostic elements, such as fluorescence, to permit sophisticated cellular analysis and counting (such as CBC with 5-part WBC differential). It is further contemplated that embodiments of the invention may be adapted to provide a low-cost fluorescence activated cell sorter (FACS).

For convenience in this disclosure, the invention will generally be described with reference to its use as a particle detector. Such description is not intended to limit the scope of the instant invention in any way. It is recognized that certain embodiments of the invention may be used simply to detect passage of particles, e.g. for counting. Other embodiments may be structured to determine particle characteristics, such as size, or type, thereby permitting discrimination analyses. Furthermore, for convenience, the term "fluid" may be used herein to encompass a fluid mix including a fluid base formed by one or more diluents and particles of one or more types suspended or otherwise distributed in that fluid base. Particles are assumed to have a characteristic "size", which may sometimes be referred to as a diameter, for convenience. Currently preferred embodiments of the invention are adapted to interrogate particles found in whole blood samples, and this disclosure is structured accordingly. However, such is not intended to limit, in any way, the application of the invention to other fluids including fluids with particles having larger or smaller sizes, as compared to blood cells.

In this disclosure, "single-file travel" is defined different than literally according to a dictionary definition. For purpose of this disclosure, substantially single-file travel may be defined as an arrangement of particles sufficiently spread apart and sequentially organized as to permit reasonably accurate detection of particles of interest. In general, we shoot for single particle detection at least about 80% of the time. When two particles are in the interrogation zone at the same, it is called coincidence, and there are ways to mathematically correct for it. Calibration may be performed using solutions having a known particle density (e.g. solutions of latex beads having a characteristic size similar to particle(s) of interest). Also, dilution of the particles in a fluid carrier may contribute to organizing particle travel. As a non-limiting example, it is currently preferred to use sensor devices structured to have sizes disclosed in this document for interrogation of fluid samples having a particle density of approximately between about $3 \times 10^3$ to about $3 \times 10^5$ cells/ml, where the particle size is on the order of the size of a red blood cell.

FIG. 1 illustrates certain operational details of a currently preferred sensor component, generally indicated at 100, structured according to certain principles of the instant invention. As illustrated, sensor 100 includes a sandwich of five layers, which are respectively denoted by numerals 102, 104, 106, 108, and 110, from top-to-bottom. A first portion 112 of a conduit to carry fluid through the sensor component 100 is formed in layer 108. Portion 112 is disposed parallel to, and within, the layers. A second portion 114 of the fluid conduit passes through layer 106, and may be characterized as a tunnel. A third portion 116 of the fluid conduit is formed in layer 104. Fluid flow through the conduit is indicated by arrows 118 and 118'. Fluid flowing through the first and third portions flows in a direction generally parallel to the layers, whereas fluid flowing in the second portion flows generally perpendicular to the layers.

It is within contemplation that two or more of the illustrated layers may be concatenated, or combined. Rather than carving a channel out of a layer, a channel may be formed in a single layer by machining or etching a channel into a single layer, or by embossing, or folding the layer to include a space due to a local 3-dimensional formation of the substantially planar layer. For example, illustrated layers 102 and 104 may be combined in such manner. Similarly, illustrated layers 108 and 110 may be replaced by a single, concatenated, layer.

With continued reference to FIG. 1, middle layer 106 carries a plurality of electrodes arranged to dispose a plurality of electrodes in a 3-dimensional array in space. Sometimes, such electrodes are arranged to permit their electrical communication with electrical surface connectors disposed on a single side of the sandwich, as will be explained further below. As illustrated, fluid flow indicated by arrows 118 and 118' passes over a pair of electrodes 120, 122, respectively. However, in alternative embodiments within contemplation, one or the other of electrodes 120, 122 may not be present. Typically, structure associated with flow portion 114 is arranged to urge particles, which are carried in a fluid medium, into substantially single-file travel through an interrogation zone associated with one of, or both of, electrodes 120, 122. Electrodes 120, 122 may sometimes be made reference to as interrogation electrodes. In certain applications, an electrical property, such as a current, voltage, resistance, or impedance indicated at $V_A$ and $V_B$, may be measured between electrodes 120, 122, or between one of, or both of, such electrodes and a reference.

Certain sensor embodiments employ a stimulation signal based upon driving a desired current through an electrolytic fluid conductor. In such case, it can be advantageous to make certain fluid flow channel portions approximately as wide as possible, while still achieving complete wet-out of the stimulated electrodes. Such channel width is helpful because it allows for larger surface area of the stimulated electrodes, and lowers total circuit impedance and improves signal to noise ratios. Exemplary embodiments used to interrogate blood samples include channel portions that are about 0.10" wide and about 0.003" high in the vicinity of the stimulated electrodes.

One design consideration concerns wettability of the electrodes. At some aspect ratio of channel height to width, the electrodes MAY not fully wet in some areas, leading to unstable electrical signals and increased noise. To a certain point, higher channels help reduce impedance and improve wettability. Desirably, especially in the case of interrogation electrodes, side-to-side wetting essentially occurs by the time the fluid front reaches the second end of the electrode along the channel axis. Of course, wetting agents may also be added to a fluid sample, to achieve additional wetting capability.

Still with reference to FIG. 1, note that electrodes 120 and 122 are illustrated in an arrangement that promotes complete wet-out of each respective electrode independent of fluid flow through the tunnel forming flow portion 114. That is, in certain preferred embodiments, the entire length of an electrode is disposed either upstream or downstream of the tunnel forming flow portion 114. In such case, the "length" of the electrode is defined with respect to an axis of flow along a portion of the conduit in which the electrode resides. The result of such an arrangement is that the electrode is at least substantially fully wetted independent of tunnel flow, and will therefore provide a stable, repeatable, and high-fidelity signal with reduced noise. In contrast, an electrode having a tunnel passing through itself may provide an unstable signal as the wetted area changes over time. Also, one or more bubble may be trapped in a dead-end, or eddy-area disposed near the tunnel (essentially avoiding downstream fluid flow), thereby variably reducing the wetted surface area of a tunnel-penetrated electrode, and potentially introducing undesired noise in a data signal.

In general, disposing the electrodes 120 and 122 closer to the tunnel portion 114 is better (e.g., gives lower solution impedance contribution), but the system would also work with such electrodes being disposed fairly far away. Similarly, a stimulation signal (such as electrical current) could be delivered using alternatively structured electrodes, even such as a wire placed in the fluid channel at some distance from the interrogation zone. The current may be delivered from fairly far away, but the trade off is that at some distance, the electrically restrictive nature of the extended channel will begin to deteriorate the signal to noise ratios (as total cell sensing zone impedance increases).

With continued reference to FIG. 1, electrode 124 is disposed for contact with fluid in conduit flow portion 112. Electrode 126 is disposed for contact with fluid in flow portion 116. It is currently preferred for electrodes 124, 126 to also be carried on a surface of interrogation layer 106, although other configurations are also workable. Note that an interrogation layer, such as an alternative to illustrated single layer 106, may be made up from a plurality of sub-component layers. In general, electrodes 124, 126 are disposed on opposite sides of the interrogation zone, and may sometimes be made reference to as stimulated electrodes. In certain applications, a signal generator 128 is placed into electrical communication with electrodes 124 and 126 to input a known stimulus to the sensor 100. However, it is within contemplation for one or both of electrodes 124, 126 to not be present in alternative operable sensors structured according to certain principles of the instant invention. In alternative configurations, any electrode in the sensor 100 may be used as either a stimulated electrode or interrogation electrode.

Figure 2:
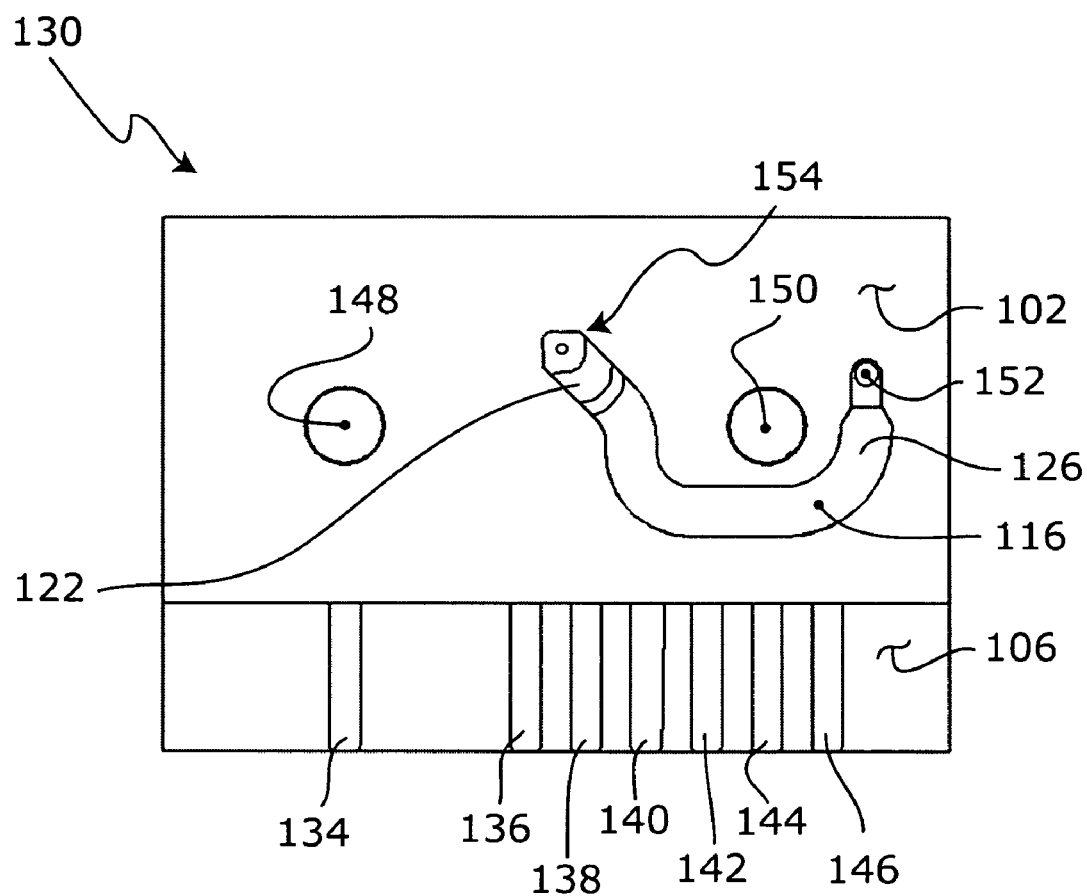
FIG. 2 is a top view of an exemplary multi-layer sensor component.

One currently preferred sensor component, generally indicated at 130, will now be described with reference to FIGS. 2-5. Sensor 130 includes five thin film layers stacked to form a thin film sandwich, similar to the embodiment depicted in FIG. 1. FIG. 2 is a top view of sensor component 130, and shows how the top cap layer 102 and top channel layer (e.g. 104, FIG. 3) form a window arranged to permit access to a portion of interrogation layer 106. In the illustrated embodiment, the exposed portion includes an edge of layer 106. The exposed surface of the edge of interrogation layer 106 carries a plurality of conductors (134 through 146, respectively) that are configured to form an electrical interface to interrogation circuitry. That is, a portion of each of conductors 134-146 is desirably exposed to form a plurality of surface connectors of an electrically communicating interface. One operable such interface may be formed in harmony with a commercially available multi-pin electrical connector, such as part No. SIB-110-02-F-S-LC, available from Samtec having a place of business located in New Albany, Ind. Other workable connector structure includes touch-down probes, and other electrically-conductive, contact-forming probes known in the art.

Also shown in FIG. 2 are alignment holes 148 and 150, respectively. Because top layer 102 is illustrated as being transparent (although such is not required for practice of the invention), electrode 126 disposed in channel portion 116 is visible. Similarly, fluid via 152 may be seen. As will be detailed further below, via 152 passes through interrogation layer 106, and permits fluid flow downwardly through the thickness of the sensor component 130. Electrode 122 is also visible, disposed in association with the interrogation zone, generally indicated at 154.

Figure 3:
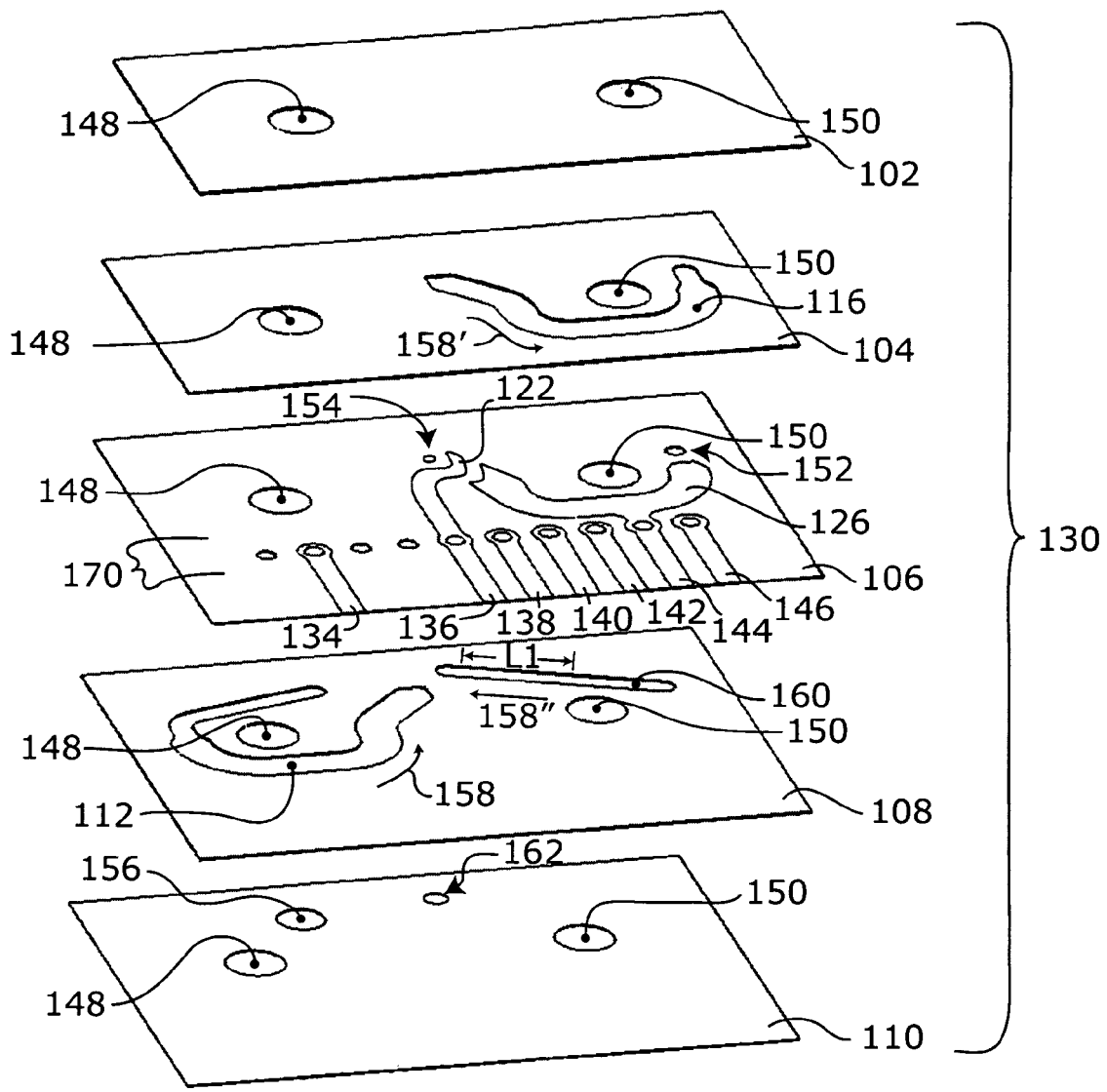
FIG. 3 is an exploded assembly view in perspective from above of the multi-layer sensor component of FIG. 2.
Figure 4:
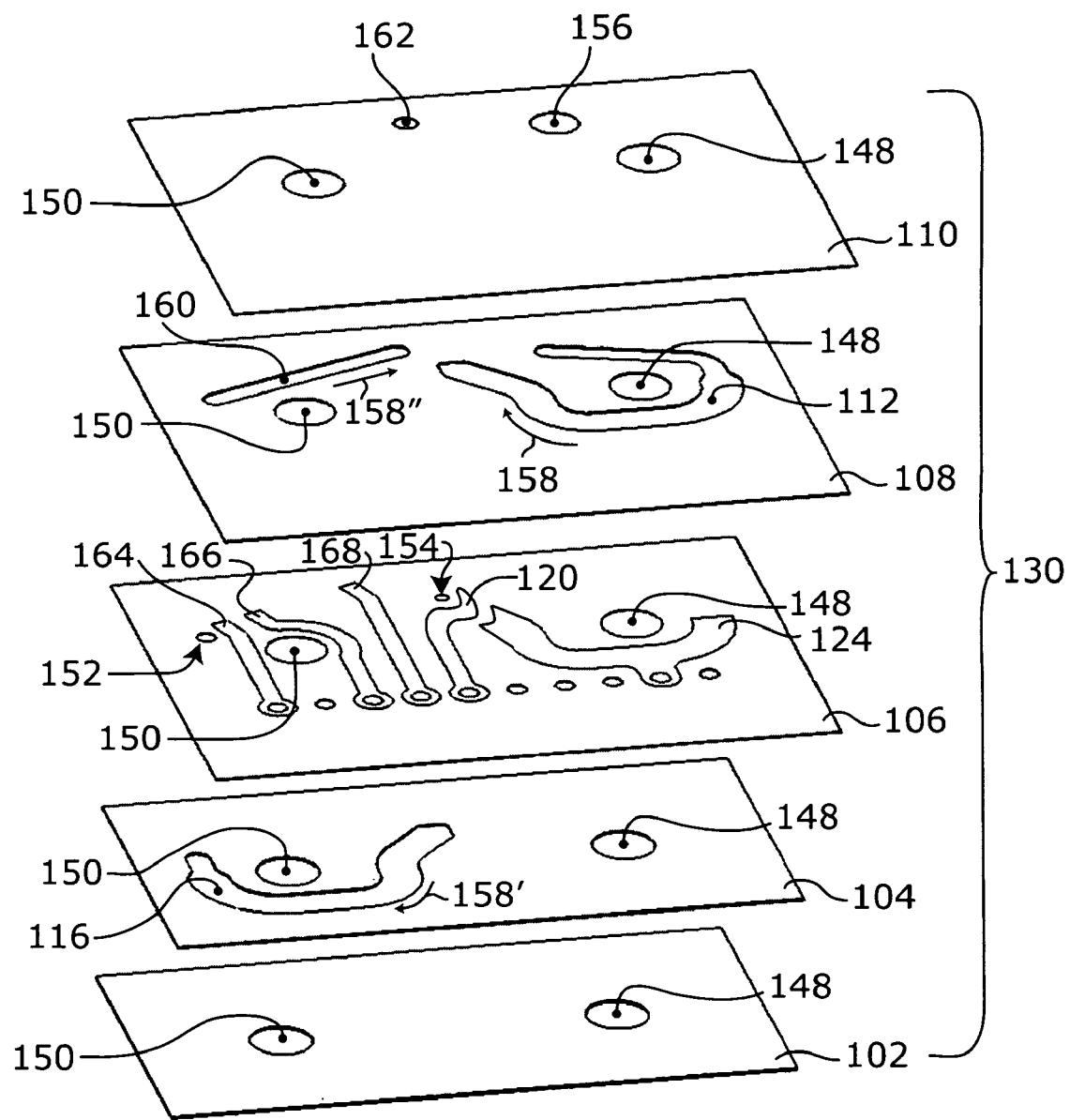
FIG. 4 is an exploded assembly view in perspective from below of the multi-layer sensor component of FIG. 2.

With particular reference now to FIGS. 3 and 4, a pair of fluid vias pass through bottom cap layer 110. Via 156 is a fluid entrance via, through which sample fluid enters the sensor component 130 for continued flow through channel portion 112, as indicated by fluid flow direction arrow 158. Channel portion 112 is disposed in layer 108 and introduces fluid into the interrogation zone 154 (or tunnel-like channel portion 114 in FIG. 1). Downstream from the interrogation zone 154, fluid flows through channel portion 116 as indicated by fluid flow direction arrow 158'. Channel portion 116 is disposed in layer 104 and communicates to via 152 passing through layer 106. Fluid via 152 communicates fluid into channel portion 160 disposed in layer 108. Fluid via 162 is a fluid exit via, through which fluid flowing through channel portion 160 may leave the sensor component 130. A direction of fluid flow in channel 160 is indicated by arrow 158".

Figure 5:
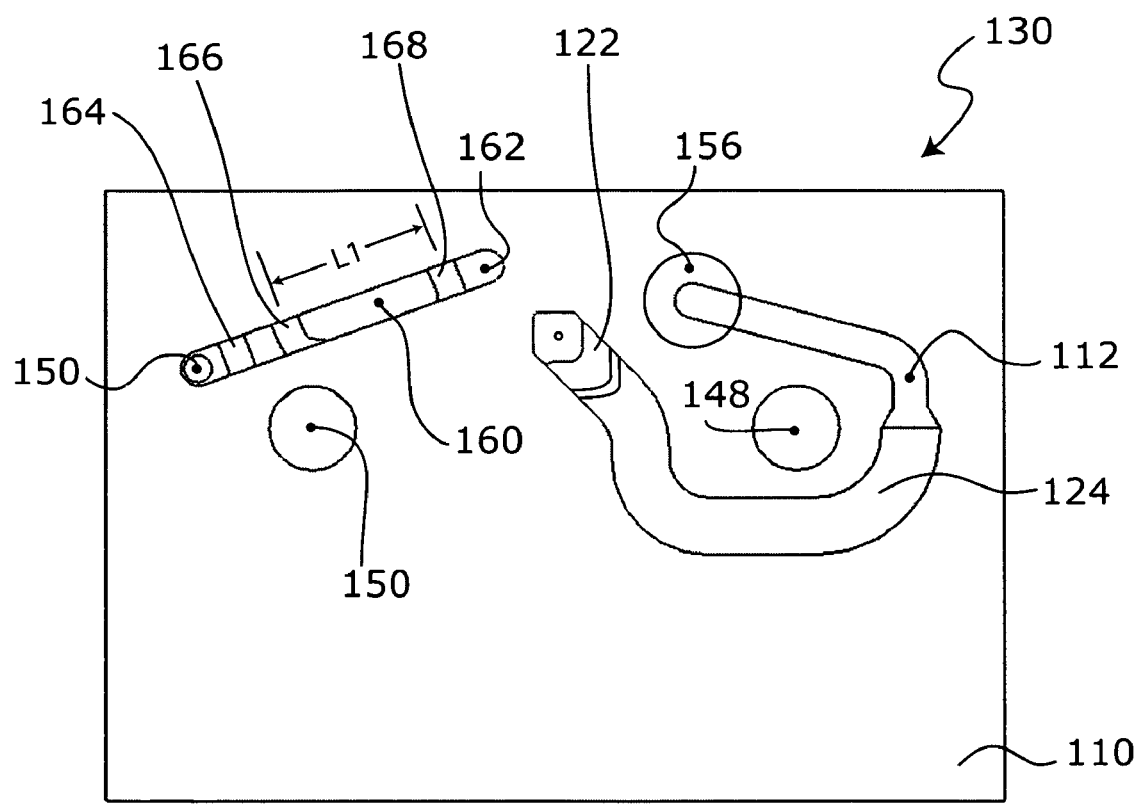
FIG. 5 is a bottom view of the multi-layer sensor component of FIG. 2.

As best seen with reference to FIGS. 4 and 5, certain embodiments of a sensor component 130 may include one or more additional and optional electrodes. Layers 102 and 104 are illustrated as being transparent, although such is not required for practice of the invention. As illustrated, electrodes 164, 166, and 168 are disposed on layer 106 and are arranged for contact with fluid carried in channel portion 160. Electrode 164 is in electrical communication with conductor 146; electrode 166 is in electrical communication with conductor 142; and electrode 168 is in electrical communication with conductor 140. Such optional electrodes may be used, for examples, to verify the presence of sample fluid at one or more known locations in sensor 130, to estimate the rate of fluid flow through the sensor, and/or as start or stop triggers for an activity such as data acquisition.

It should be noted that certain electrodes carried by sensor 130 (e.g. 120, 124, 164-168), are in electrical communication with their respective conductor that is disposed on an opposite side of layer 106 by way of a conductive path disposed through a respective electrical via 170 (see FIG. 3). Such conductive path is conveniently formed during a laminating or metallizing step during manufacture of the sensor component. In any case, it should be appreciated that a complex pattern of electrodes can be disposed to interrogate fluid in 3-dimensional space, even in the illustrated case where the electrodes are carried by a single metallized layer.

The conductive elements forming conductors (e.g. 134-146) and/or electrodes (e.g. 120-126) must simply conduct electricity, and can include one or more metal, such as Copper, Silver, Platinum, Iridium, Chromium, and Gold, or alloys, or multiple layers of metals or alloys. The vias 170 permit conduction of electricity from top to bottom through spacer layer 106, and enable surface conductors to be disposed on only one side of the spacer layer, for convenient interface with a commercially available electrode interface (i.e. connector). Of course, it is realized that certain interface probe-electrodes of an interrogation platform may be structured to avoid vias on the sensor, e.g. that surface electrodes can be provided on both sides of the spacer layer, in alternative sensor constructions.

An electrical property at an electrode may be monitored to determine arrival of fluid at that electrode. For example, the impedance measured at an electrode undergoes a significant change in value as the wave-front, or the leading edge, an electrolyte fluid passes over the electrode. In one currently preferred use of the sensor component 130 (see FIG. 4), a stimulus electric signal (such as a 1 kHz square wave) is applied to electrode 164. A sudden change in the impedance values measured at electrodes 166 and 168 indicates the successive arrivals of the wave-front of the sample fluid at each respective electrode. In the illustrated embodiment 130, first verification of fluid at electrode 166 ensures that sample fluid is in place for interrogation, and a test run can begin. Feedback from electrode 166 may therefore serve as a first trigger to begin interrogation of the fluid sample.

A change in impedance at electrode 168 indicates the wave-front has reached that electrode as well. A time differential between the impedance changes at electrodes 166 and 168 can be used, in harmony with a known volume therebetween, to estimate a fluid flow rate through the sensor component 130. The volume between electrodes 166 and 168 may be calculated by integrating the function of the cross-section area of channel portion 160 along the length L1 of such channel portion disposed between those electrodes. It is currently preferred to simplify such calculation by holding the cross-section of channel portion 160 constant between electrodes.

Electrodes, such as 166 and 168, may be disposed as first and second triggers operable to indicate respective start and stop signals based upon detection of a fluid boundary. The first and second triggers can be located to have locations of effective operation that are disposed spaced apart by a lumen defining a known volume. Such triggers may be used, for non-limiting example, to start and stop data acquisition for a sample having a known volume. It is preferred for cooperating trigger electrodes to have substantially the same conformation (e.g. wetted area and axial length), to promote consistent electrical response of each subsequent downstream trigger. Sometimes, the channel may be narrowed in the vicinity of an electrode to reduce possible variations in the shape of the fluid front as it makes contact with the electrode.

A sensor 130 may be formed from a plurality of stacked and bonded layers of thin film, such as a polymer film. In an exemplary sensor component 130 used in connection with interrogation of blood cells, it is currently preferred to form top and bottom layers 102 and 110 from Polyamide or Mylar film. A workable range in thickness for Polyamide layers is believed to be about 0.1 micron to about 500 microns. A currently preferred Polyamide layer 102, 110 is about 52 microns in thickness. It is further within contemplation that a pair of top and/or bottom layers can be formed from a single layer including fluid channel structure formed e.g. by etching, molding, or hot embossing.

It is currently preferred to make the spacer layer 106 from Polyamide also. However, alternative materials, such as Polyester film or Kapton, which is less expensive, are also workable. A film thickness of about 52 microns for spacer layer 106 has been found to be workable in a sensor used to interrogate blood cells. Desirably, the thickness of the spacer layer is approximately on the order of the particle size of the dominant particle to be interrogated. A workable range is currently believed to be within about 1 particle size, to about 15 times particle size, or so.

Vias 170 are typically formed in the layer 106 prior to dual-sided deposition of the conductive elements onto such layer, although alternative manufacturing techniques are workable. Alignment apertures 148, 150 and via 152 may be formed at the same time as vias 170, or subsequent to the metallizing step. Such void elements, and channel portions, may be formed by cutting through the respective layer with a laser, water jet, die stamping, drilling, or by some other machining technique. Deposition of conductive film elements to layer 106 may be effected using well-known metal-deposition techniques, including lamination. Metal sheets may be laminated to a polymer layer using thin adhesive. Double clad sheets formed in such manner are commercially available, and can be patterned as desired to form electrodes. It is believed that workable sensors can be made having test electrodes that are 0.5 microns in thickness, or perhaps even less. Electrodes for use in currently preferred blood cell sensors may be up to about 36 microns in thickness. Sometimes, a pair of metals, such as Cu or Cr and Au may be deposited in the current process. The Cu or Cr layer may be thin, typically goes on first, and acts as a bonding layer between the polymer film and the Au. It is currently preferred to configure the electrodes and conductive elements by wet etching subsequent to deposition of the electrically conductive material.

Impedance at the electrode/electrolyte interface is proportional to wetted electrode surface. Electrodes may be configured having a desired useful size of surface area disposed for contact with fluid in a channel. It is currently preferred to apply a stimulation signal to stimulated electrodes to cause at least about 0.1 mA RMS current flow through the interrogation zone. The currently preferred signal is at 100 kHz, although signals at lower frequency or higher frequencies, such as 200 k Hz, or more, are operable. The surface area of the stimulated electrodes are sized to accommodate a desired current flow and signal frequency. It is currently believed that electrodes should be sized to have a current density of less than about 5 mA/cm$^2$.

In one embodiment of sensor 130 adapted to impart a constant 1 mA RMS current stimulation at about 100 kHz, interrogation electrodes 120, 122 have a wetted surface area of about 0.036 cm$^2$, and stimulated electrodes 124, 126 have a wetted surface area of about 0.45 cm$^2$. In such case, it is thought that the stimulated electrodes 124, 126 could be reduced in size to about ⅕ cm$^2$, or less, without suffering a lack of performance due to degradation of the electrode during such stimulation.

The channel portion 114 is typically laser drilled through layer 106 (and any electrodes carried thereon that are also disposed in the fluid path). A diameter of 35 microns for channel 114 is currently preferred to urge blood cells toward single-file travel through the interrogation zone 154. Other cross-section shapes, other than circular, can also be formed during construction of channel 114. Naturally, the characteristic size of the orifice formed by drilling channel 114 will be dependent upon the characteristic size of the particles to be characterized or interrogated. Counter-boring can be performed on thicker layers to reduce the "effective thickness" of the sensing zone.

Alignment holes 148, 150 passing through each layer may be used to align the various layers using guide pins during assembly of the plurality of layers. A double-sided adhesive polymer film is currently preferred as a material of composition for combination bonding-channel layers 104 and 108. Layers 104 and 108 in a currently preferred sensor 130 are made from double-sided Polyamide (PET) tape having a thickness of about 0.0032 inches. Alternatively, a plain film layer may be laminated to an adjacent plain layer using heat and pressure, or adhesively bonded using an interposed adhesive, such as acrylic or silicone adhesive.

Figure 6:
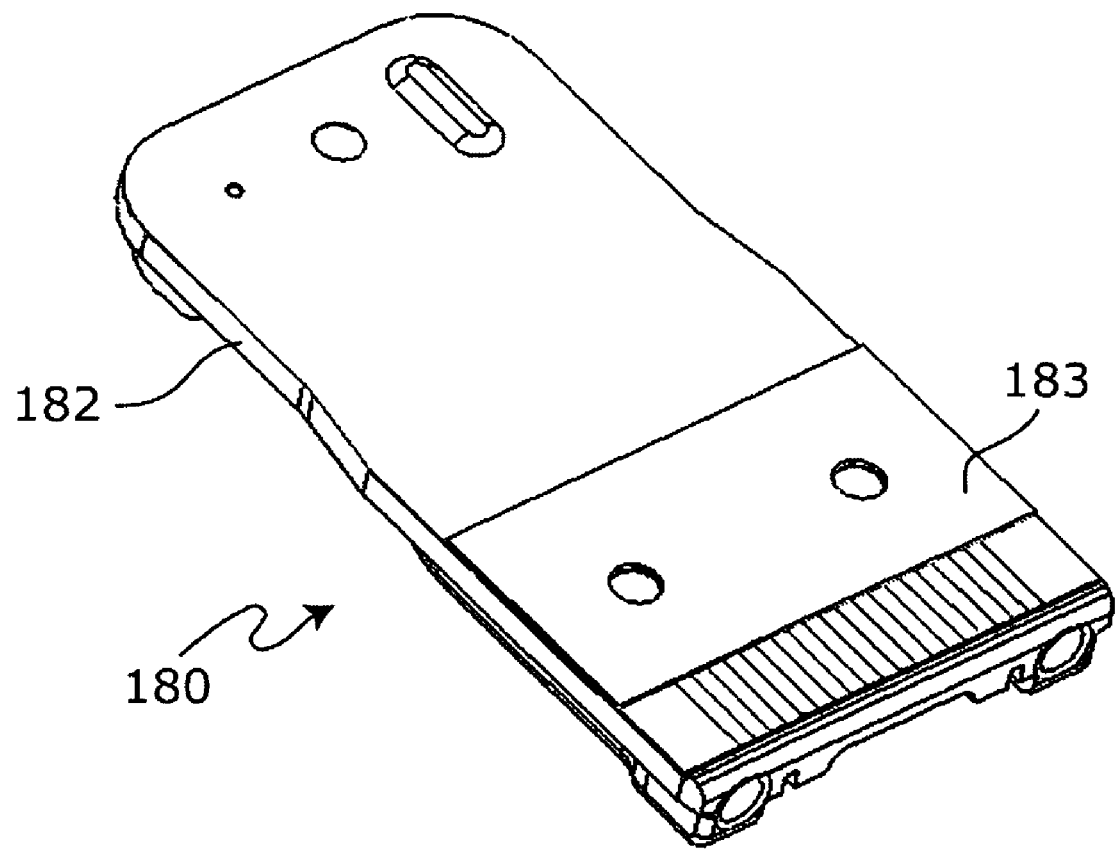
FIG. 6 is a view in perspective from above of a sensor component carried by a cartridge.

A currently preferred sensor structured according to certain principles of the instant invention is generally indicated at 180 in FIG. 6, and may sometimes be characterized as a cartridge. Cartridge 180 includes a base 182 on which to hold a sensor component, such as some sort of thin film sensor 183. A workable base may be formed by injection molding a plastic, or plastic-like, material. It is preferred to configure base 182 having a small size to reduce a required volume of constituent material, but still form a sensor 180 that is sufficiently large to facilitate its handling and manipulation under control of a human hand.

Figure 7:
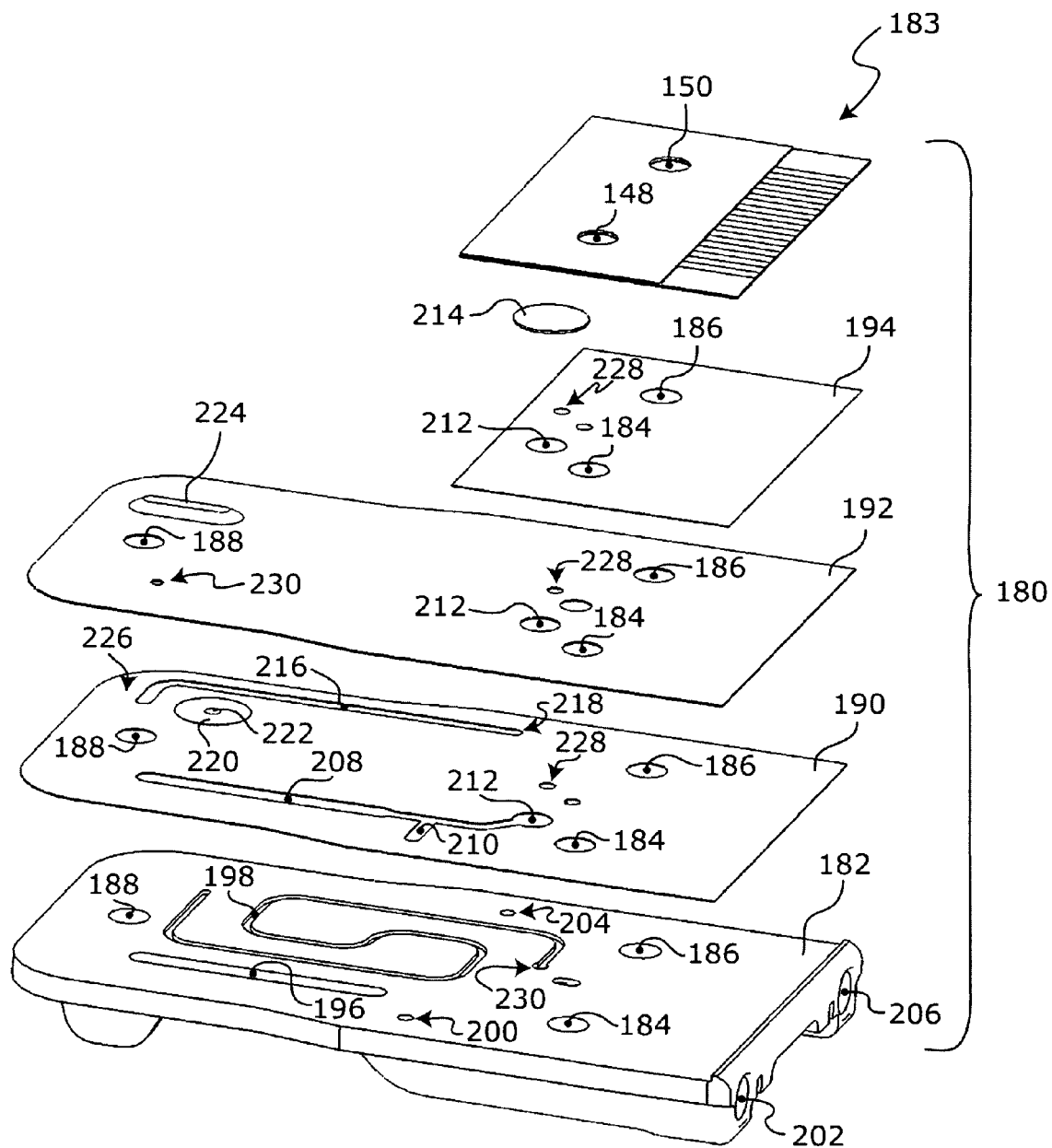
FIG. 7 is an exploded assembly view in perspective from above of the cartridge of FIG. 6.
Figure 8:
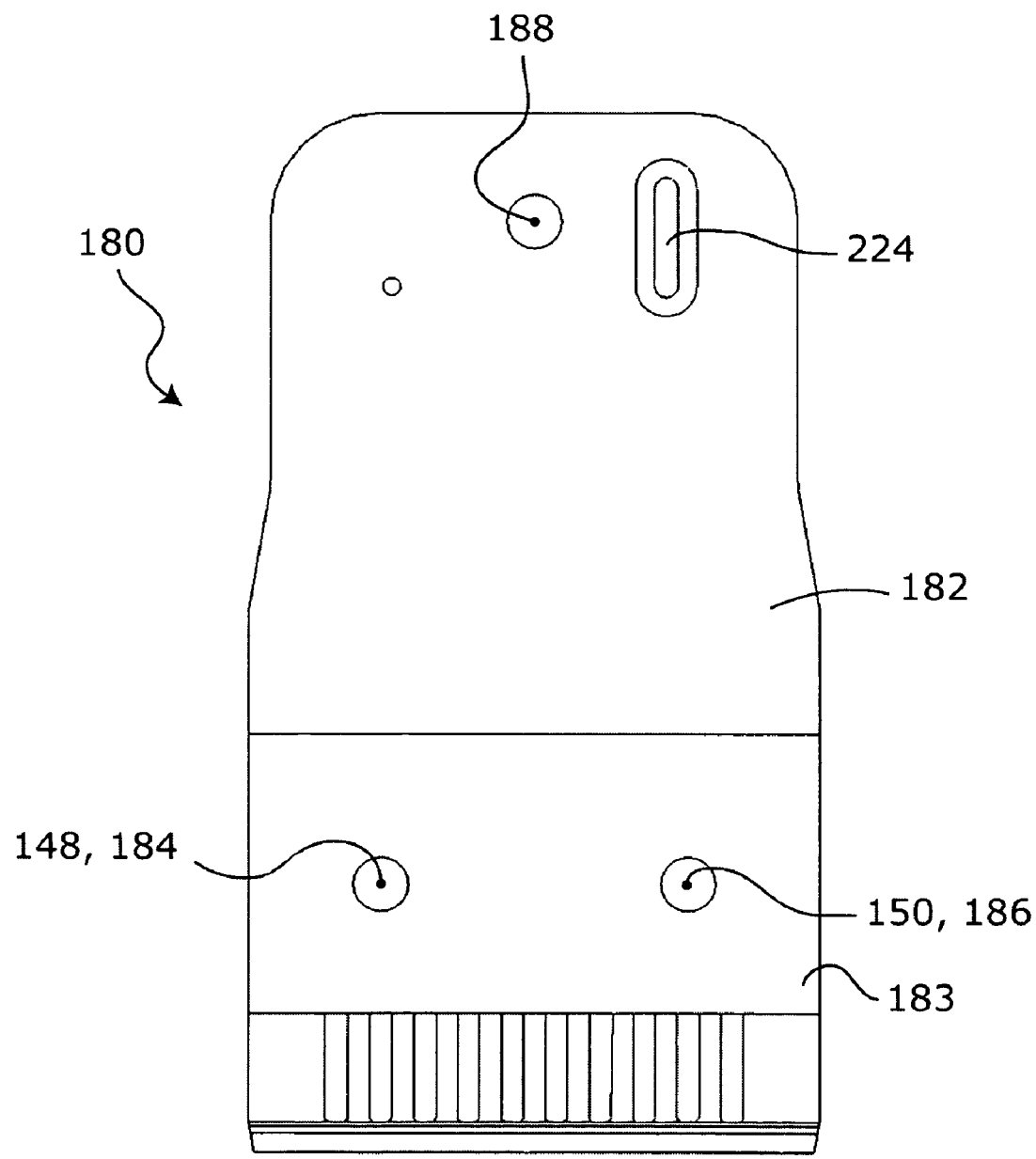
FIG. 8 is a top view of the cartridge of FIG. 6.
Figure 9:
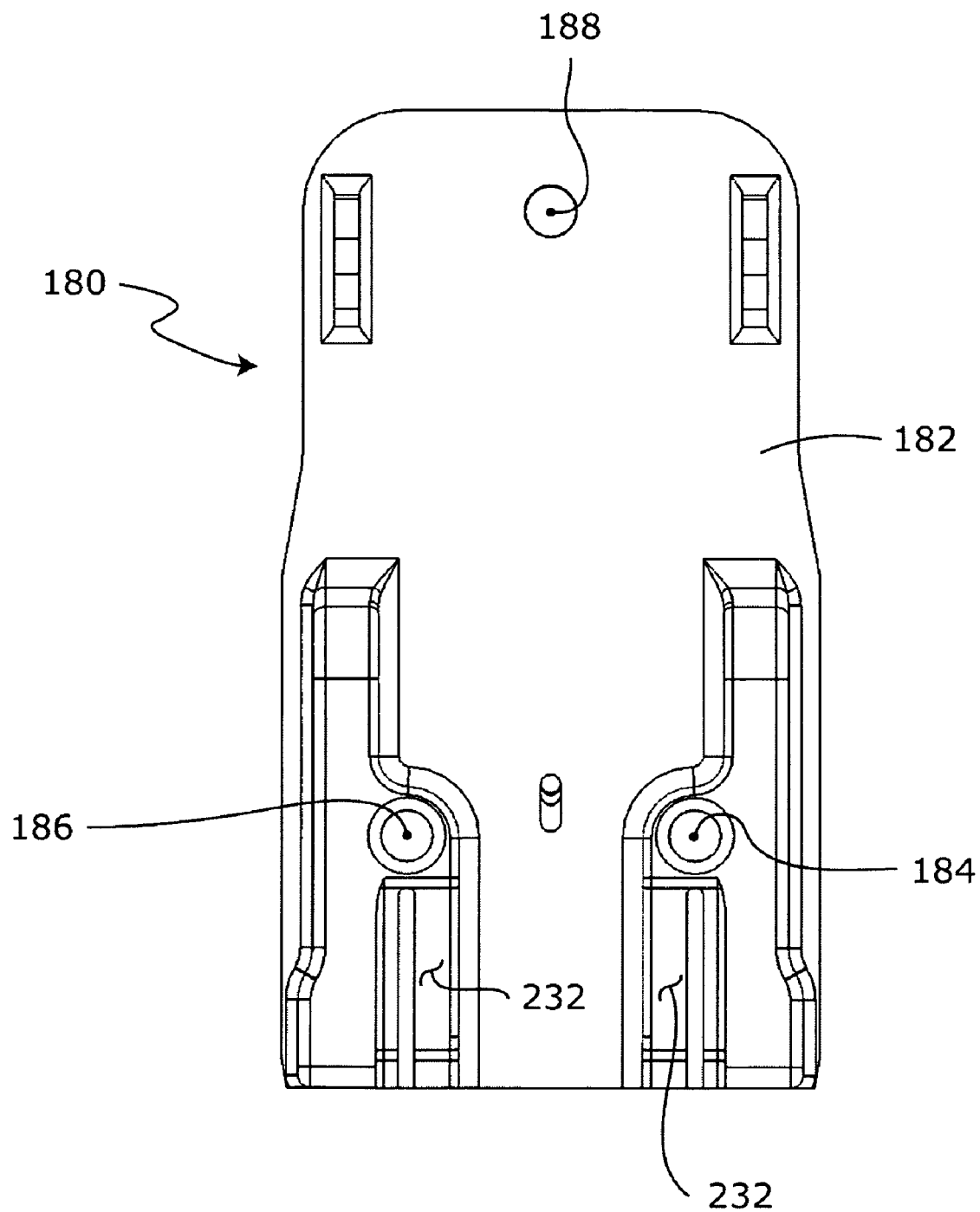
FIG. 9 is a bottom view of the cartridge of FIG. 6.
Figure 10:
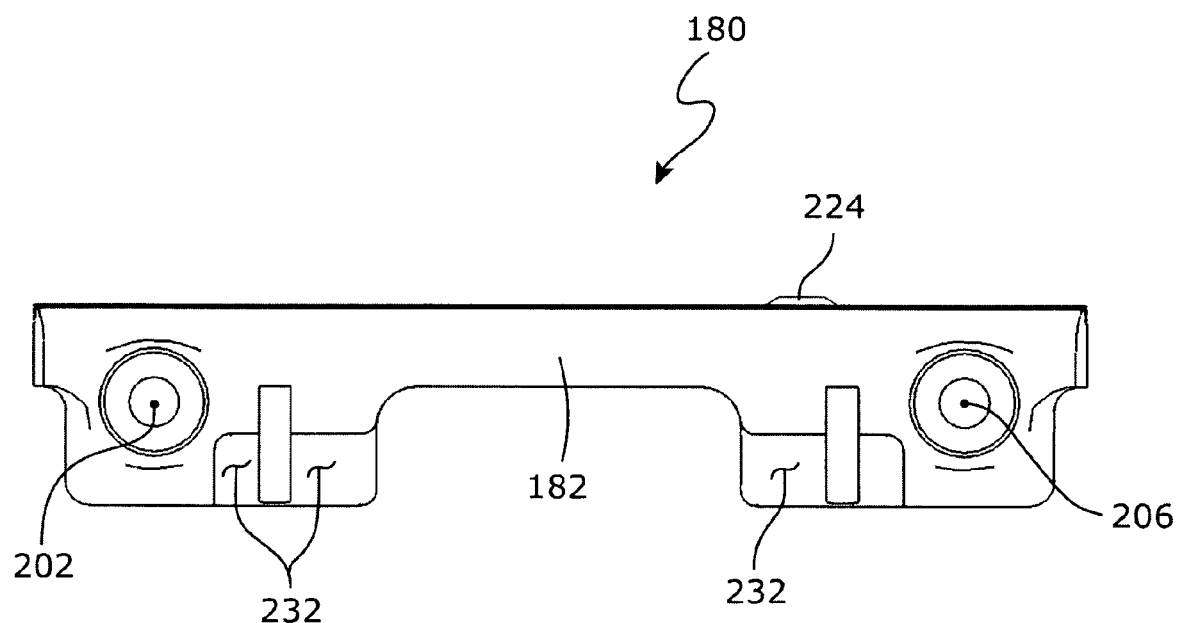
FIG. 10 is an end view of the cartridge of FIG. 6.
Figure 11:
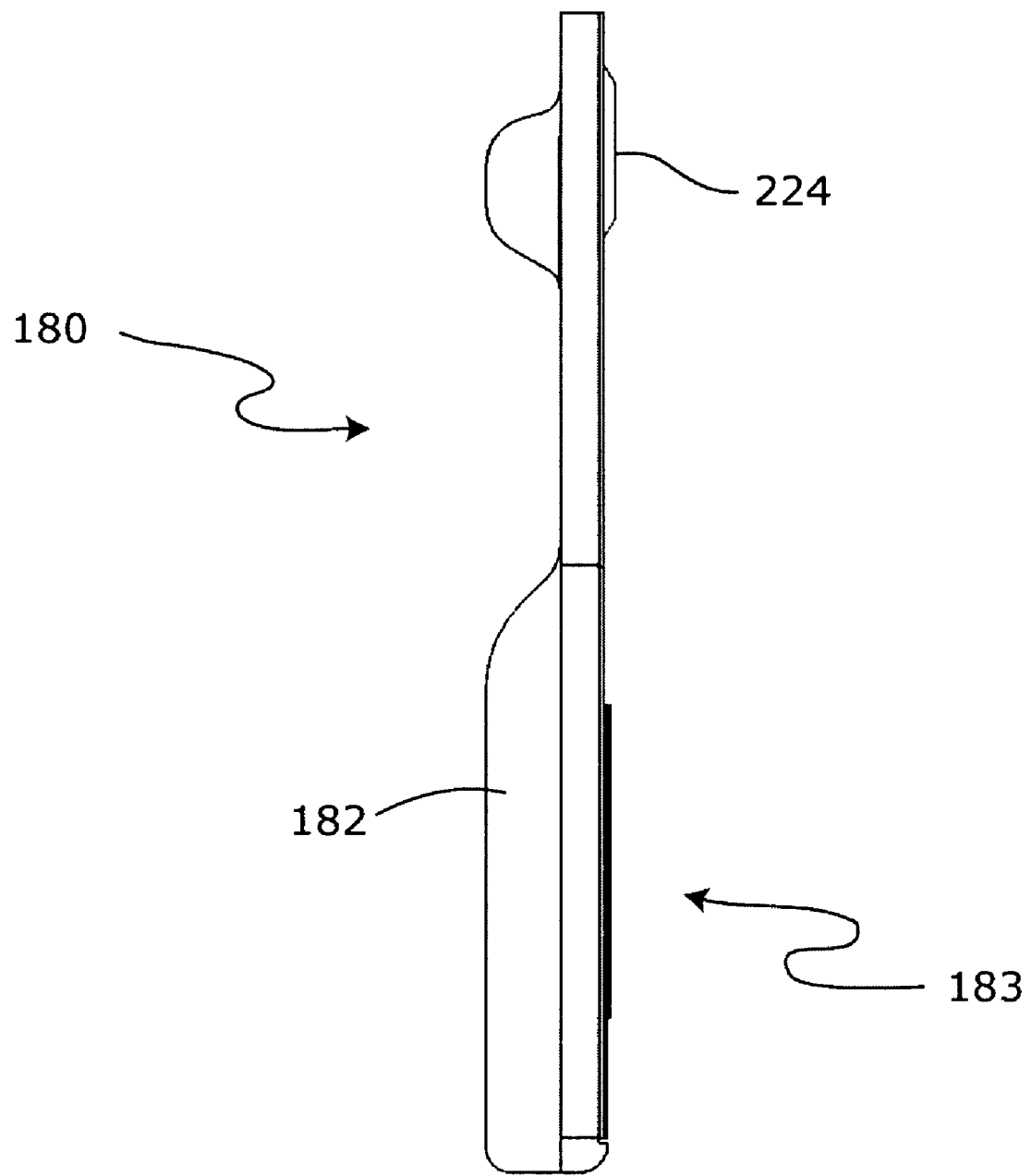
FIG. 11 is a side view of the cartridge of FIG. 6.
Figure 14:
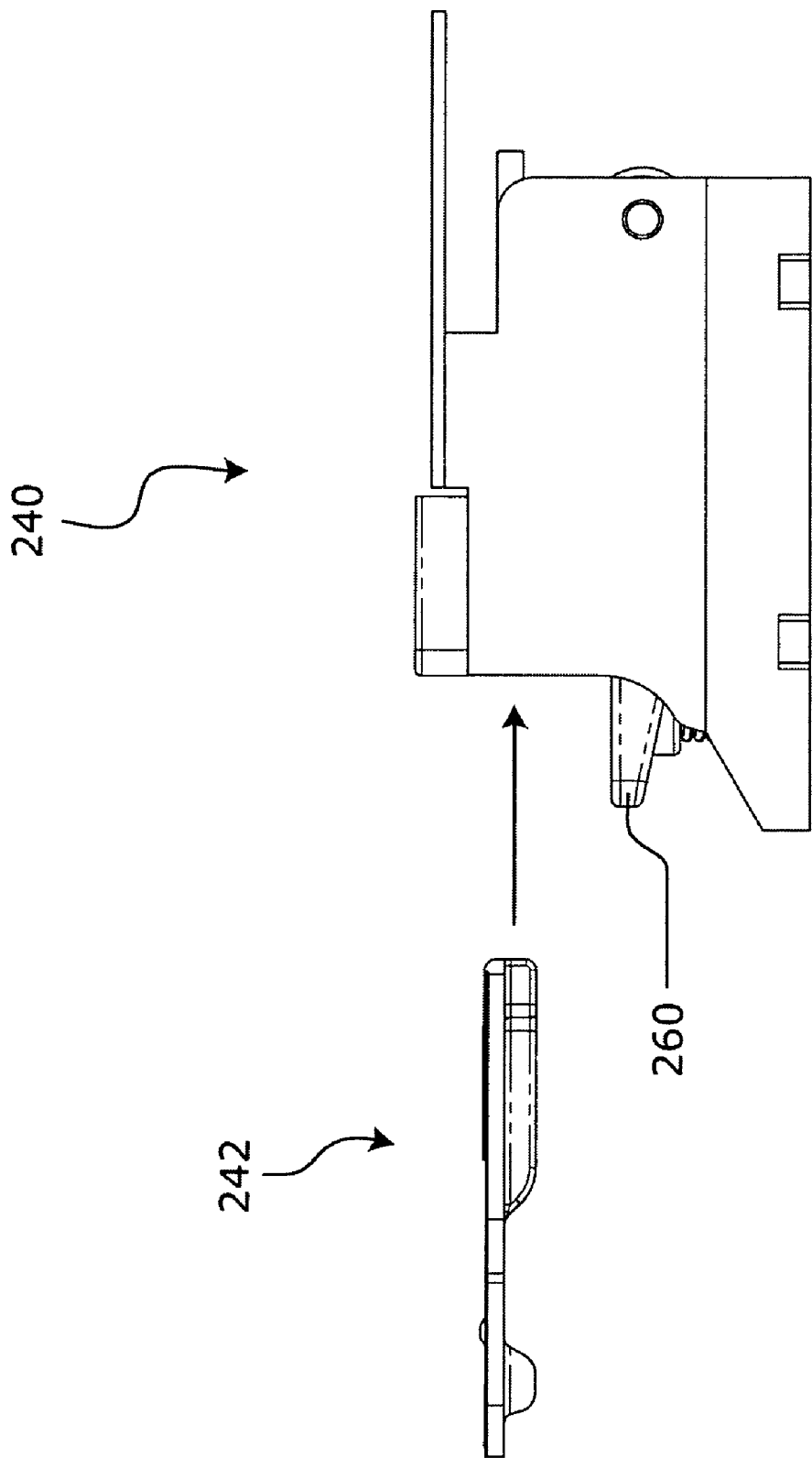
FIG. 14 is a side view of the assembly of FIG. 12.
Figure 15:
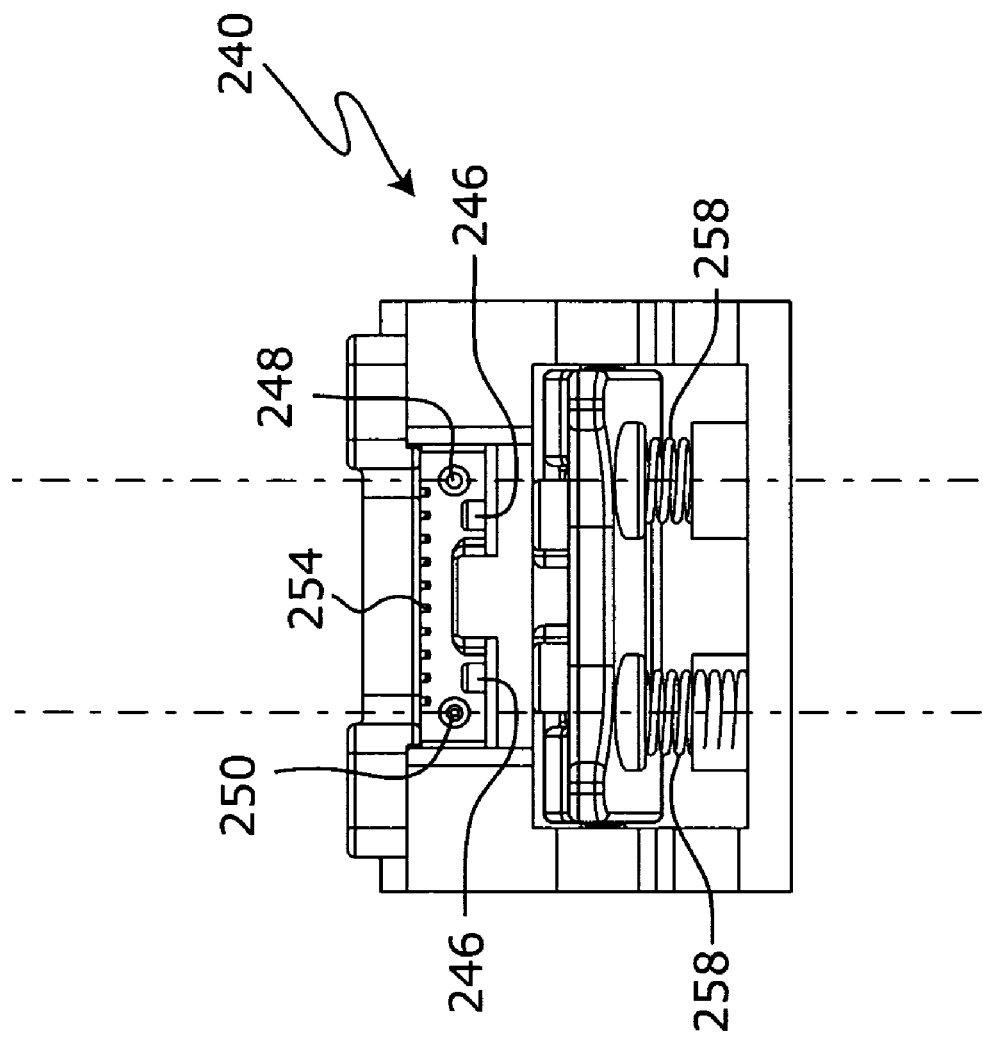
FIG. 15 is a cartridge-loading end view of the interrogation platform of FIG. 12.

With reference now to FIG. 7, base element 182 includes alignment holes 184, 186, and 188, which also extend to pass through channel layer 190, cap layer 192, and adhesive layer 194. Holes 184 and 186 are configured and arranged to cooperate with alignment holes 148 and 150, respectively, to permit component alignment using pin elements of a common fixture during assembly of the sensor 180. Base element 182 also holds sample receiving chamber 196, and processed fluid chamber 198. Vent aperture 200 is in fluid communication through base 182 with vent connection access port 202. Similarly, vacuum aperture 204 is in fluid communication through base 182 with vacuum connector access port 206.

Channel layer 190 may be formed from a thin film of polymer film, similar to layers 104, 108 of the sensor 130. Preferably, layer 190 is made from a two-sided adhesive tape, such as Polyamide tape. Layer 190 includes cut-out area shaped to form additional void elements, including channel 208, a portion of which augments a volume provided by chamber 196 in which to receive a fluid sample. Transverse portion 210 of channel 208 communicates to vent aperture 200, effective to permit escape of air from chamber 196 during infusion of a sample for interrogation.

Continuing to refer to FIG. 7, aperture 212 extends as a fluid-flow channel or via through layers 190, 192 and 194 effective to introduce fluid received from chamber 196 into sensor component 183. An optionally enlarged portion of channel 212 permits fluid to spread out over a sufficiently large filter area prior to passing through optional filter element 214 and entering sensor element 183. It typically is desirable to include a filter element 214 to resist entrance into the interior of sensor component 183 of clots or debris that might plug channel portion 114. A preferred filter element 214 resists passage of particles larger than those approaching the characteristic size of the interrogation zone 154. A workable filter 214 includes a Nylon Net Filter NY30 available from Millipore Cat: NY3004700, which has filtering pores that are about 30 microns in size. Desirably, the filter essentially consists of openings having a characteristic size that is smaller than a characteristic size of a minimum cross-section of the interrogation zone.

Still with reference to FIG. 7, layer 190 also includes vacuum channel 216, which communicates at end 218 with vacuum aperture 204. As will be discussed in more detail below, fluid may be transported through certain conduits of sensor 180 using a vacuum source that may be connected to port 206.

In certain preferred embodiments, a barrier element 220 is disposed in association with aperture 222 passing through layer 190. A workable barrier element 220 permits escape of air from chamber 198, but resists escape of fluid from such chamber. A preferred barrier 220 includes a PTFE gasket, such as a 0.2 micron pore size Fluoropore, FGLP, which can be purchased from Millipore Cat. No. FGLP01300. Gasket 220 is illustrated in FIG. 7 as being installed in a preferred blocking position on the bottom of layer 190, but may be disposed in a blocking position on either side of layer 190. Barrier 220 is an exemplary embodiment of flow termination structure disposed downstream from the interrogation zone and arranged to resist flow of fluid beyond a boundary associated with the microfluidic sensor. Other operable flow termination structure includes porous materials that turn to gels when wet; hydrophobic porous membranes or plugs; and very small laser drilled holes in films (e.g. <10 microns).

Continuing to refer to FIG. 7, an exemplary layer 192 may be made from polymer film, and functions as a cap layer, similar to layer 110 of sensor component 183. An embossed portion 224 is formed in layer 192 to create a simple channel structure through which air can communicate between end 226 of vacuum channel 216 and aperture 222. The vacuum-side fluid conduit communicating between port 206 and a sensor exit (such as exit via 162 of sensor 130), is completed by way of aperture 228, which forms a fluid conduit or via extending from end 230 of chamber 198, through layers 190, 192, and 194, for communication with a fluid exit via of an installed thin film sensor component 183.

In use of the device, a micro-pipette tip may be inserted for fluid-tight reception into sample-receiving aperture or port 230. A raw fluid sample can then be infused from the micro-pipette into chamber 196, while air is permitted to escape through channel 210 and vent port 202. The size for a raw fluid sample for characterization of blood cells in a representative device is 50 µl, although the sensor conduits and chambers may be sized to accommodate samples having an alternative desired size. Vent port 202 is then occluded, either manually or using an automated structure. A vacuum source is then applied to port 206 to promote fluid flow from holding chamber 196, through channel 208, aperture 212, optional filter 214, and into a fluid entrance of the sensor component.

After flowing through the sensor component, fluid is drawn through aperture 228 and into holding chamber 198. Once chamber 198 is filled, fluid is barred from further flow by barrier element 220, which is one example of operable flow termination structure that resists additional flow. The volume of fluid encompassed by chamber 198 can help to determine a known volume for processed fluid. In the representative device, the processed fluid volume, defined by chamber 198 in combination with a small upstream volume contained in conduit structure stretching to a fluid-front presence verification structure, such as electrode 166 (see FIG. 4), is 25 µl.

Additional details of construction of an exemplary cartridge 180 are illustrated in FIGS. 8-11. Notably, ramp structure 232, best seen in FIGS. 9 and 10, can be helpful to assist in coupling the cartridge with certain interrogation platforms. Other structure associated with the base 182, such as alignment holes 186 and 188, may also be employed to assist in coupling a cartridge with an interrogation platform.

An interrogation platform desirably provides three functions; 1) electrical continuity to the sensor, 2) fluid-flow control, and 3) alignment. A workable, and currently preferred interrogation platform is indicated generally at 240 in FIGS. 12-15.

A cartridge 242 is illustrated in position for its insertion in registration with socket 244 (see FIG. 13). As the cartridge is inserted into the socket 244, ramps 232 on the bottom side of the cartridge body press the two alignment pins 246 down. The cartridge 242 then comes into contact with the vent and vacuum connectors, 248 and 250, respectively.

In the illustrated platform 240, the vent connector 248 and vacuum connector 250 are made from silicone rubber tubing. The rubber tubes mate with respective connection ports (e.g. 202 and 206, see FIG. 10) to form an airtight seal. The silicone rubber tubing is supported on the inside by a smaller, more ridge piece of tubing. The rigid, internal tubing imparts the required mechanical stability while the soft, flexible rubber tubing conforms to make an airtight seal. This airtight seal is actually made because the rubber tube extends sufficiently to contact the bottom of the cartridge mating hole before the cartridge is fully seated. When the cartridge is inserted slightly further into the interrogation platform, the rubber tube is forced to expand radially outward, thereby making an airtight seal against its receiving socket (e.g. 202 or 206).

When seated in socket 244, the electrical contact pads (on the top of the cartridge and generally indicated at 252 in FIG. 12) contact biased pins 254 of the electrical connector 256. The electrical connector 256 places the sensor 242 in electrical communication with test circuitry 257 that is typically carried by an interrogation platform and is adapted to interrogate particles passing through the sensor.

When the cartridge 242 is fully inserted, the alignment pins 246 seat inside the alignment holes 184, 186 in the bottom of the cartridge via force imparted by springs 258. The cartridge is now fully engaged, aligned, and ready for testing. To remove a cartridge, the release latch 260 is pressed downward, thereby retracting the alignment pins 246 from the cartridge body as the latch rotates about pivot axle 262. The cartridge can then be easily pulled out of the interrogation platform.

The interrogation platform may include circuitry that may be carried on printed circuit board 264, or otherwise arranged to communicate with the sensor. A plurality of different test circuits may be provided by simply exchanging the circuit board to one having the desired configuration. Such circuitry may include structure arranged to apply a first time-varying stimulus signal to stimulated electrodes. A currently preferred first stimulus signal is a constant current source, although a constant voltage source is also workable. A preferred first stimulus signal is about 100 kHZ 1 mA rms. A second stimulus signal may be provided and coupled to electrodes adapted to detect presence of a fluid wave-front. A preferred second signal is a 1 k Hz square wave input to a first electrode and permitting measurement of an electric property by using at least one other electrode. Impedance or voltage may be evaluated at or between measurement electrodes. Sometimes, a differential may be measured between electrodes. Other times, ground may be enforced at one electrode, and an electrical property measured at the other electrode. It is within contemplation for one electrode to be eliminated entirely, and use a ground reference.

Figure 16:
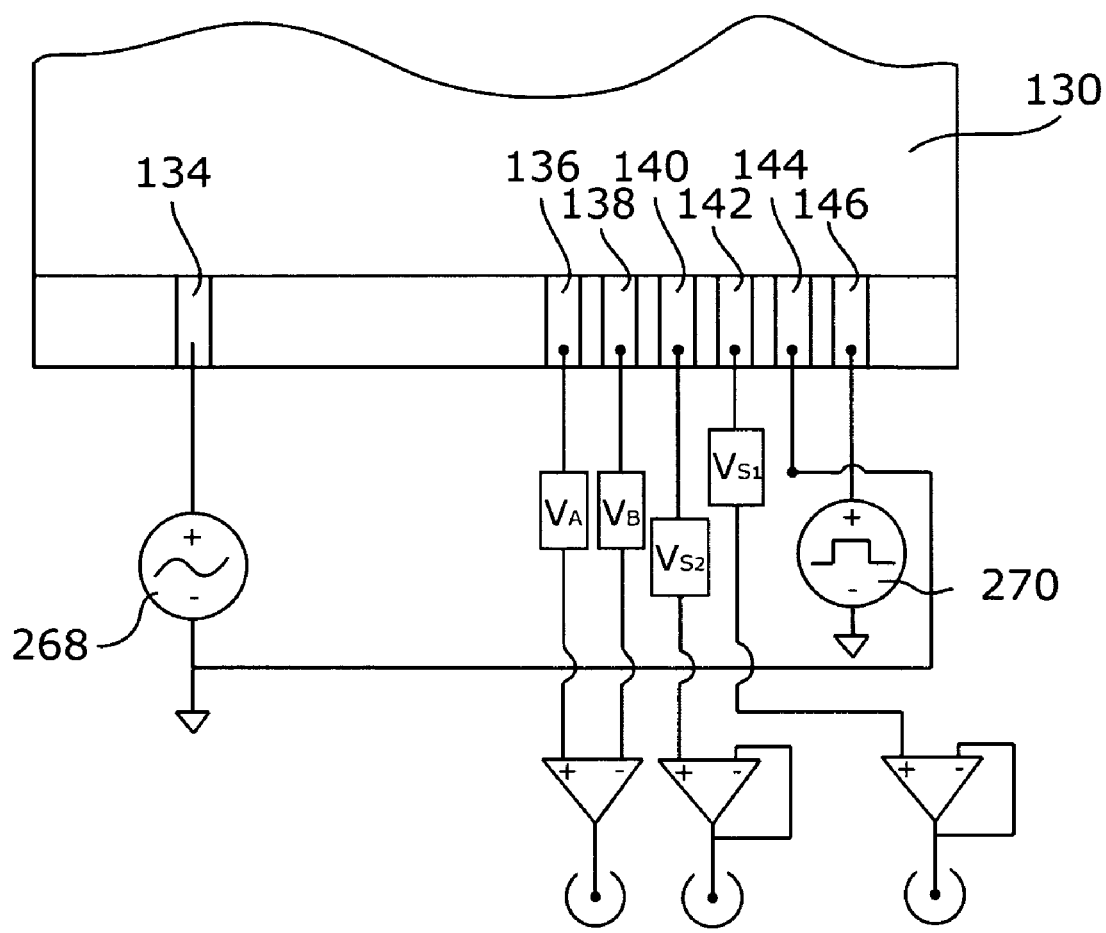
FIG. 16 is a schematic of a workable interrogation circuit for use with a sensor such as illustrated in FIG. 6.
Figure 17:
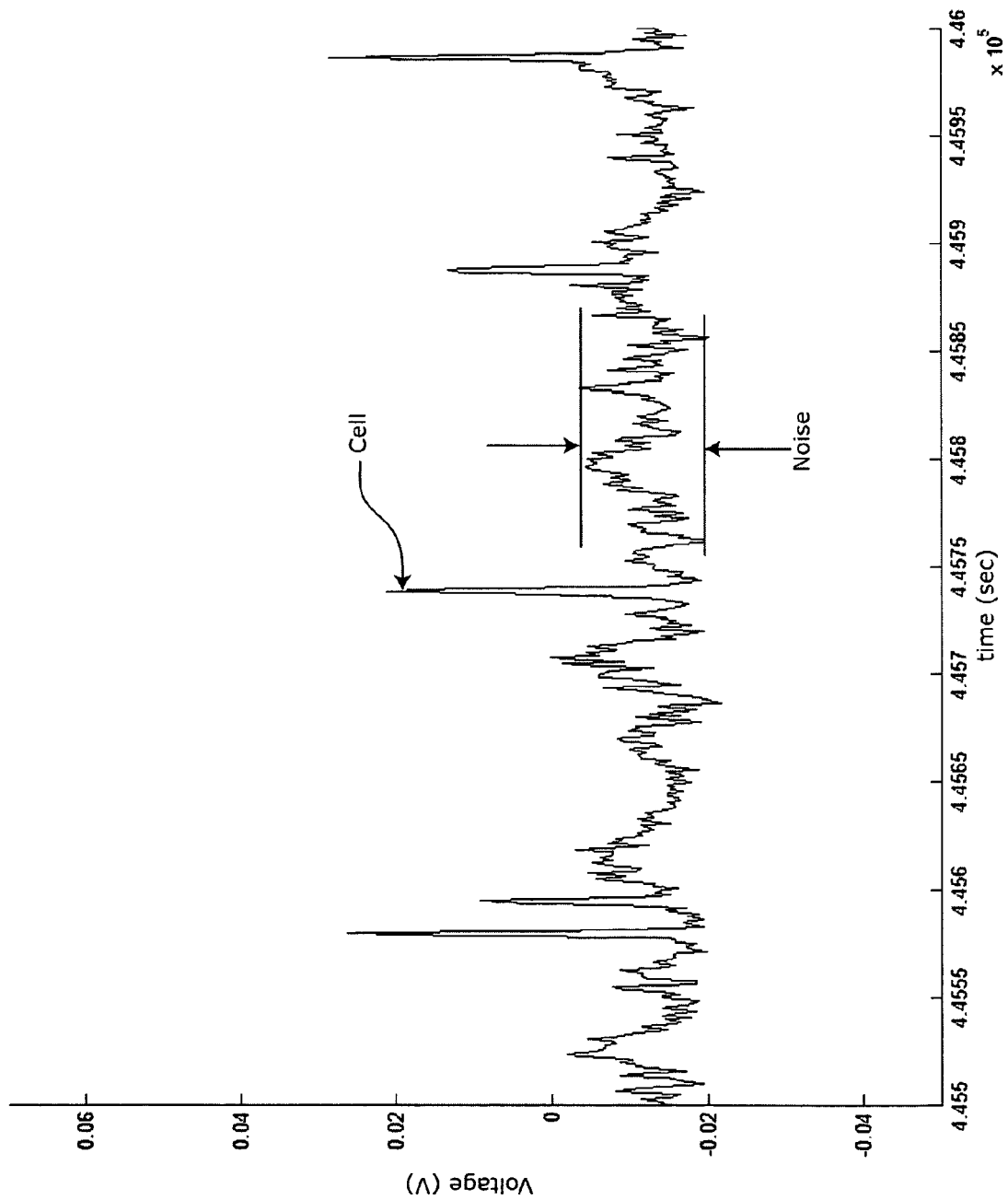
FIG. 17 is an X-Y plot of certain interrogation data.
Figure 18:
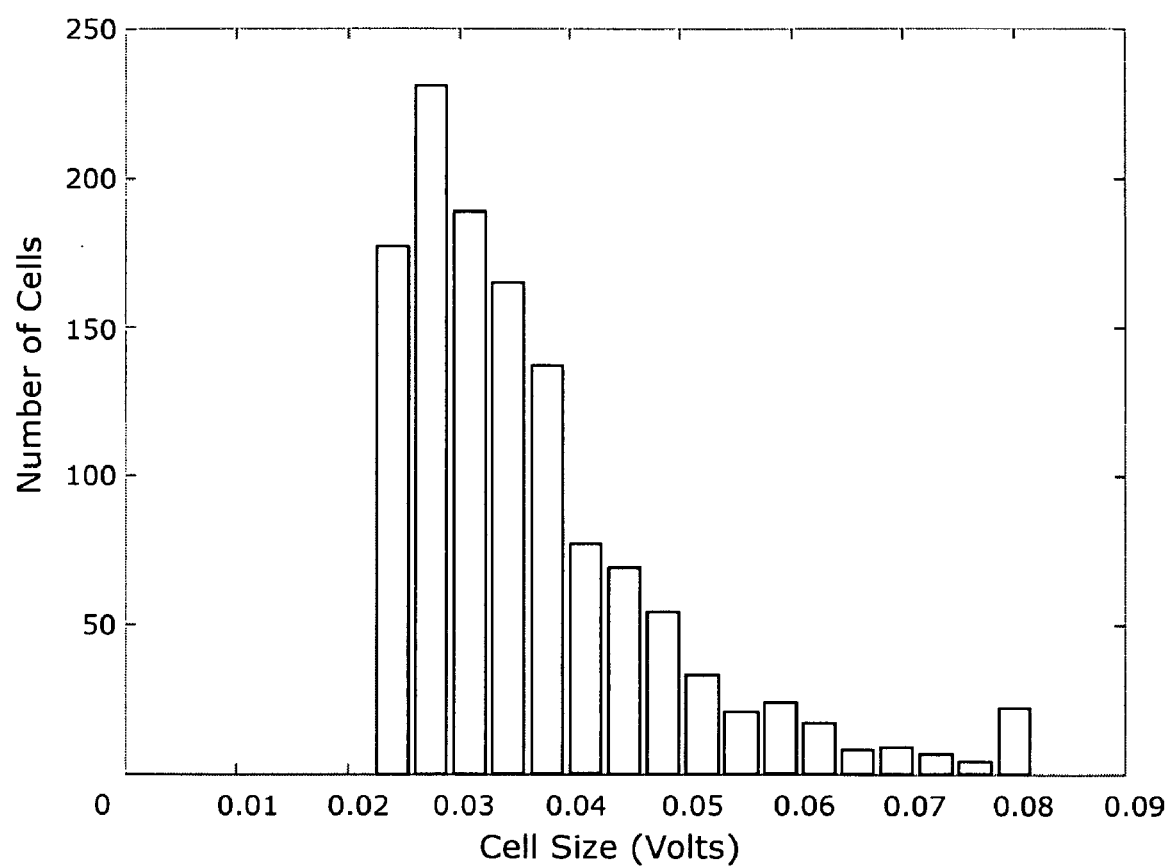
FIG. 18 is a bar chart depicting certain collected data.

FIG. 16 illustrates one workable interrogation circuitry adapted to interrogate a sensor 130. In the cell interrogation loop, a signal generator 268 is applied between conductors 134 and 144. It has been determined that electrical ground may be enforced at one of such conductors. In current sensors adapted to interrogate blood cells, it is preferred to apply a constant RMS current signal of about 1 mA at about 100 kHz. Values for voltages $V_A$ and $V_B$ are measured at conductors 136 and 138, respectively for calculation of a differential voltage across the cell interrogation zone. It has been determined that an electrical ground may be enforced at one such conductor, and the voltage directly measured at the other conductor may be used in place of a true differential voltage. It is also possible to allow one electrode to "float" (i.e. not be connected to anything) and measure the voltage from the other electrode. In the fluid detection loop, a signal generator 270 is applied between conductor 146 and each of conductors 140 and 142. The impedance or voltage signal $V_{S1}$ and $V_{S2}$ are measured to determine the presence of the fluid wave-front. A sudden drop in the measured impedance indicates presence of the wave-front of electrolytic fluid. A workable signal includes a square-wave at about 1 kHz at about 3 volts. FIGS. 17 and 18 present data that may be collected using the disclosed sensors.

In a method of using the device to count cells in a blood sample, 50 micro-liters of fluid are added to the sensor via the pipette-tip hole which is sized to form an air tight fit with the pipette tip. As the sample enters the sample storage channel, air displaced by the fluid exits the cartridge through a vent port that connects to the interrogation platform. The sample can be added to the cartridge before or after it has been connected to the interrogation platform. Once the sample is in the cartridge, and the cartridge is installed in an interrogation platform, the user starts the test by activating one or more "start" control of the system. The "start" causes a valve connected to the vent port to close, thereby not allowing the sample to flow into the vent port. The "start" also opens the vacuum valve to start pulling the fluid sample into the sensor. Because the vent is sealed, fluid is drawn from the sample storage chamber and though the thin film sensor component. A "start" may also initiate a stimulus (e.g. 1 kHz) to the sample detection electrodes embedded in the thin film sensor component. Once the fluid is through the sensing orifice and has wet the stimulus and measurement electrodes, it flows over a pair of sample detection electrodes. As the fluid wavefront reaches the detection position at the second electrode, a large drop in electric impedance is detected and the constant current source is activated (e.g. 100 kHz @ 1 mA). A differential voltage is measured across the interrogation zone (4 electrode configuration, currently preferred) and used to determine cell size (and/or count) subsequent to the time of wave-front detection. Fluid continues to flow until it reaches the end of the "dead-end" channel and no more cells are detected. The volume that is processed in a test run is determined by the volume accommodated downstream of the wave-front detection location, and is 25 micro-liters in a preferred device. The method may also include monitoring one or more additional sample detection electrode placed further down the channel, i.e. to determine the approximate flow rate during, or prior to starting, the cell counting.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A microfluidic sensor, comprising:
   a plurality of stacked thin film substantially planar layers, certain of said layers carrying one or more electrode to dispose a plurality of electrodes in a 3-dimensional array in space; and
   a fluid path, disposed inside said sensor, comprising:
   a first portion disposed parallel to, and within, said layers;
   a second portion provided by a tunnel passing through at least one layer, a constriction in said tunnel being sized to urge particles entrained in a carrier fluid into substantially single-file travel through a particle interrogation zone; and
   a third portion disposed parallel to, and within, said layers, said first portion and said third portion being disposed on opposite sides of said particle interrogation zone.

2. The sensor according to claim 1, further comprising:
   a particle filter disposed upstream of said interrogation zone, said particle filter consisting essentially of openings having a characteristic size that is smaller than a characteristic size of a minimum cross-section of said interrogation zone.

3. The sensor according to claim 1, further comprising:
flow termination structure disposed downstream from said interrogation zone, said flow termination structure being arranged to resist flow of fluid beyond a boundary associated with said microfluidic sensor.

4. The sensor according to claim 1, further comprising:
holding structure adapted to receive a quantity of sample fluid effective to define a volumetric size of a processed sample, said holding structure comprising a dead-end chamber defining, in harmony with trigger structure of said sensor, a known volume and being vented through a fluid barrier effective to resist further flow of fluid through said sensor subsequent to filling of said chamber.

5. The sensor according to claim 1, wherein:
an interrogation layer of said sensor comprises said at least one layer; and
at least one electrode is carried on each of top and bottom surfaces of said interrogation layer.

6. The sensor according to claim 5, further comprising:
a plurality of electrical surface connectors individually disposed in electrical communication with selected ones of each of said electrodes; wherein:
all of said electrical surface connectors are disposed on a single side of said interrogation layer.

7. The sensor according to claim 1, further comprising:
a first trigger and a second trigger operable to indicate respective start and stop signals based upon detection of a fluid boundary, said first trigger and said second trigger having respective locations of effective operation that are disposed spaced apart by a lumen defining a known volume.

8. The sensor according to claim 7, wherein:
said first trigger comprises:
 a first electrode disposed to contact fluid flowing through said sensor; and
 a second electrode disposed to contact fluid flowing through said sensor, wherein:
 said first trigger is structured to permit detecting impedance between said first electrode and said second electrode.

9. The sensor according to claim 8, wherein:
said second trigger comprises:
 said first electrode; and
 a third electrode disposed to contact fluid flowing through said sensor, wherein:
 said second trigger is structured to permit detecting impedance between said first electrode and said third electrode.

10. The sensor according to claim 1, further comprising:
a first stimulated electrode disposed for contact with fluid in said first portion;
a second stimulated electrode disposed for contact with fluid in said third portion; and
a first interrogation electrode disposed for contact with fluid between said first stimulated electrode and said second stimulated electrode.

11. The sensor according to claim 10, wherein:
a second interrogation electrode is disposed between said first stimulated electrode and said second stimulated electrode.

the entire length of said first interrogation electrode, measured along an axis of said first portion, is disposed upstream of said tunnel; and
the entire length of said second interrogation electrode, measured along an axis of said third portion, is disposed downstream of said tunnel.

12. The sensor according to claim 10, wherein:
the entire length of said first interrogation electrode, measured along an axis of said third portion, is disposed downstream of said tunnel.

13. The sensor according to claim 10, wherein:
said first stimulated electrode and said second stimulated electrode each have a surface area, disposed for contact with fluid in said fluid path, greater than about $1/10$ cm$^2$.

14. The sensor according to claim 10, wherein:
the entire length of said first interrogation electrode, measured along an axis of said first portion, is disposed upstream of said tunnel.

15. The sensor according to claim 10, further comprising:
a second interrogation electrode disposed between said first stimulated electrode and said second stimulated electrode.

16. The sensor according to claim 15, wherein:
the entire length of said second interrogation electrode, measured along an axis of said third portion, is disposed downstream of said tunnel.

17. A multi-layer microfluidic sensor, comprising:
a first fluid-flow channel formed in a first layer, said first fluid-flow channel being configured to permit fluid flow in a direction generally parallel to said first layer;
a first electrode disposed for contact with fluid in said first fluid-flow channel;
a second electrode disposed downstream of said first electrode, said first electrode and said second electrode being carried on a first side of an interrogation layer;
a second fluid-flow channel passing through said interrogation layer, said second fluid-flow channel being sized to urge single-file travel therethrough of particles entrained in a carrier fluid; and
a third electrode, disposed for contact with fluid in a third fluid-flow channel and carried on a second side of said interrogation layer, said third fluid-flow channel being formed in a layer and configured to permit flow of fluid received from said second fluid-flow channel to continue in a direction generally parallel to a layer.

18. The sensor according to claim 17, further comprising:
flow detection structure arranged to permit estimation of rate-of-flow of sample fluid downstream from said interrogation zone.

19. The sensor according to claim 17, further comprising:
an entrance port communicating to said first fluid-flow channel; and
an exit port communicating from said third fluid-flow channel, said entrance port and said exit port being disposed on the same side of said sensor.

20. The sensor according to claim 17, further comprising:
a first trigger and a second trigger operable to indicate respective start and stop signals based upon detection of a fluid boundary, said first trigger and said second trigger having respective locations of effective operation that are disposed spaced apart by a lumen defining a known volume.

* * * * *